(12) United States Patent
Konh

(10) Patent No.: US 12,402,913 B2
(45) Date of Patent: Sep. 2, 2025

(54) STEERABLE SURGICAL DEVICES, AND METHODS FOR THEIR USE AND TRACKING

(71) Applicant: UNIVERSITY OF HAWAII, Honolulu, HI (US)

(72) Inventor: Bardia Konh, Honolulu, HI (US)

(73) Assignee: UNIVERSITY OF HAWAII, Honolulu, HI (US)

( * ) Notice: Subject to any disclaimer, the term of this patent is extended or adjusted under 35 U.S.C. 154(b) by 861 days.

(21) Appl. No.: 17/516,076

(22) Filed: Nov. 1, 2021

(65) Prior Publication Data
US 2022/0133354 A1    May 5, 2022

Related U.S. Application Data

(60) Provisional application No. 63/107,917, filed on Oct. 30, 2020.

(51) Int. Cl.
*A61B 17/34* (2006.01)
*A61B 17/00* (2006.01)

(52) U.S. Cl.
CPC ...... *A61B 17/3496* (2013.01); *A61B 17/3403* (2013.01); *A61B 2017/00867* (2013.01); *A61B 2017/3413* (2013.01)

(58) Field of Classification Search
CPC ............ A61B 17/3496; A61B 17/3403; A61B 2017/00867; A61B 2017/3413
(Continued)

(56) References Cited

U.S. PATENT DOCUMENTS 5,520,678 A    5/1996    Heckele et al.
5,919,199 A    7/1999    Mers Kelly et al.
(Continued)

FOREIGN PATENT DOCUMENTS

WO    2017147041 A1    8/2017

OTHER PUBLICATIONS

Abbott, "MitraClip Transcatheter Mitral Valve Repair," Available online at: <<https://www.vascular.abbott/us/products/structural-heart/mitraclip-mitral-valve-repair.html>>, Accessed Aug. 20, 2018, 4 pages.
(Continued)

*Primary Examiner* — Alex M Valvis
*Assistant Examiner* — Chanel J Jhin
(74) *Attorney, Agent, or Firm* — Withrow + Terranova, PLLC; Vincent K. Gustafson

(57) ABSTRACT

A steerable surgical device includes tubular body members and at least one moveable joint, with a moveable tray member arranged to permit tissue extraction and a retractable tip member for removal of a sample while a remainder of the surgical device remains in the tissue. A method utilizes sensed shape memory alloy (SMA) electrical properties and sensed compressive force to determine joint deflection that is used with a joint deflection model to map tip position in tissue. Another method for determining position of a tip of a steerable instrument within tissue utilizes transverse ultrasound probe images and image processing together with saved and predicted tip information. A method for sequentially removing a plurality of samples from tissue utilizes a steerable surgical device, without requiring complete removal of the device from the tissue.

20 Claims, 22 Drawing Sheets

(58) Field of Classification Search
USPC .......................................................... 600/567
See application file for complete search history.

(56) References Cited

U.S. PATENT DOCUMENTS

| | | | |
|---|---|---|---|
| 6,068,623 | A | 5/2000 | Zadno-Azizi et al. |
| 6,672,338 | B1 | 1/2004 | Esashi et al. |
| 7,093,086 | B1 | 8/2006 | van Rietschote |
| 8,649,847 | B1 | 2/2014 | Park et al. |
| 10,806,898 | B2 | 10/2020 | Konh |
| 2002/0026127 | A1* | 2/2002 | Balbierz ............ A61B 18/1477 600/567 |
| 2004/0044350 | A1 | 3/2004 | Martin et al. |
| 2004/0056751 | A1 | 3/2004 | Park et al. |
| 2004/0133124 | A1 | 7/2004 | Bates et al. |
| 2005/0216033 | A1 | 9/2005 | Lee et al. |
| 2007/0038230 | A1 | 2/2007 | Stone et al. |
| 2013/0345765 | A1 | 12/2013 | Brockman et al. |
| 2015/0066857 | A1 | 3/2015 | Dayal et al. |
| 2015/0133815 | A1* | 5/2015 | McGhie ............ A61B 10/0275 600/567 |
| 2015/0190123 | A1 | 7/2015 | Park et al. |
| 2015/0193248 | A1 | 7/2015 | Noel et al. |
| 2016/0124665 | A1 | 5/2016 | Jain et al. |
| 2016/0134669 | A1 | 5/2016 | Yuki et al. |
| 2016/0231944 | A1 | 8/2016 | Litke et al. |

OTHER PUBLICATIONS

Author Unknown, "MitraClip," Ehlers Danlos "Enlaces" (Argentina) blog, Available online at: <<http://ehlersdanlos-info-mas-mi-experiencia.blogspot.com/2012/07/mitraclip.html>>, Jul. 18, 2012, Accessed Aug. 20, 2018, 11 pages (webpage translated via Google).

Ayvali, E., et al., "Towards a Discretely Actuated Steerable Cannula for Diagnostic and Therapeutic Procedures," The International Journal of Robotics Research, vol. 31, Issue 5, Apr. 2012, pp. 588-603.

Black, R. J., et al., "Characterization of optically actuated MRI-compatible active needles for medical interventions," Proceedings vol. 9058, Behavior and Mechanics of Multifunctional Materials and Composites 2014, SPIE Smart Structures and Materials + Nondestructive Evaluation and Health Monitoring, 2014, San Diego, California, USA, 8 pages.

Brinson, L. C., "One-Dimensional Constitutive Behavior of Shape Memory Alloys: Thermomechanical Derivation with Non-Constant Material Functions and Redefined Martensite Internal Variable," Journal of Intelligent Material Systems and Structures, vol. 4, Apr. 1993, pp. 229-242.

Datla, N. V., et al., "A model to predict deflection of bevel-tipped active needle advancing in soft tissue," Medical Engineering & Physics, vol. 36, No. 3, Mar. 2014, pp. 285-293.

Datla, N. V., et al., "Polyacrylamide phantom for self-actuating needle-tissue interaction studies," Medical Engineering & Physics, vol. 36, No. 1, Jan. 2014, pp. 140-145.

Deuschl, F., et al., "Critical evaluation of the MitraClip system in the management of mitral regurgitation," Vascular Health and Risk Management, vol. 12, Jan. 11, 2016, pp. 1-8.

Elahinia, M. H., et al., "Control of Shape Memory Alloy Actuators," Chapter in "Shape Memory Alloy Actuators: Design, Fabrication and Experimental Evaluation," West Sussex, UK: John Wiley and Sons, Ltd., 2016.

Honarvar, M., et al., "Study of unrecovered strain and critical stresses in one-way shape memory Nitinol," Journal of Materials Engineering and Performance, vol. 23, No. 8, Aug. 2014, pp. 2885-2893.

Konh, B., "Design and Fabrication of a MirtaClip Locator Prototype for Percutaneous Transcatheter Mitral Valve Repair System," PowerPoint Presentation, Department of Mechanical Engineering, University of Hawaii at Manoa, Apr. 2017, 8 pages.

Konh, B., et al., "Design and Fabrication of a MitraClip Locator Prototype for Percutaneous Transcatheter Mitral Valve Repair System," 2017 Design of Medical Devices Conference, Apr. 10-13, 2017, Minneapolis, Minnesota, USA, 10 pages.

Konh, B., et al., "Design and Fabrication of a Robust Active Needle using SMA Wires," Design of Medical Devices Conference, Apr. 10-13, 2017, Minneapolis, Minnesota, USA, 2 pages.

Konh, B., et al., "Design optimization study of a shape memory alloy active needle for biomedical applications," Medical Engineering & Physics, vol. 37, Issue 5, May 2015, pp. 469-477.

Konh, B., et al., "Evaluating the performance of an advanced smart needle prototype inside tissue," Proceedings vol. 10164, Active and Passive Smart Structures and Integrated Systems 2017, SPIE Smart Structures and Materials + Nondestructive Evaluation and Health Monitoring, Apr. 11, 2017, 5 pages.

Konh, B., et al., "Finite element analyses of a dual actuated prototype of a smart needle," Proceedings vol. 10164, Active and Passive Smart Structures and Integrated Systems 2017, SPIE Smart Structures and Materials + Nondestructive Evaluation and Health Monitoring, Apr. 11, 2017, pp. 1-7.

Konh, B., et al., "Simulation and experimental studies in needle-tissue interactions," Journal of Clinical Monitoring and Computing, vol. 31, No. 4, Aug. 2017, pp. 861-872.

Mayo Clinic, "Mitral valve regurgitation," Available online at: <<http://www.mayoclinic.org/diseases-conditions/mitral-valve-regurgitation/symptoms-causes/dxc-20121850>>, Last updated Apr. 13, 2018, Accessed Aug. 20, 2018, 5 pages.

Merrick, G. S., et al., "Influence of timing on the dosimetric analysis of transperineal ultrasound-guided, prostatic conformal brachytherapy," Radiation Oncology Investigations, vol. 6, No. 4, May 1, 1998, pp. 182-190.

Misra, S., et al., "Mechanics of flexible needles robotically steered through soft tissue," The International Journal of Robotics Research, vol. 29, No. 13, Nov. 2010, pp. 1640-1660.

Miyano, T., et al., "Sugar micro needles as transdermic drug delivery system," Biomedical Microdevices, vol. 7, No. 3, Sep. 2005, pp. 185-188.

Morgan, N. B., "Medical shape memory alloy applications—the market and its products," Materials Science and Engineering: A, vol. 378, Issues 1-2, Jul. 25, 2004, pp. 16-23.

Nag, S., et al., "American brachytherapy society (ABS) recommendations for transperineal permanent brachytherapy of prostate cancer," International Journal of Radiation Oncology Biology Physics, vol. 44, No. 4, Jul. 1999, pp. 789-799.

Nkomo, V. T., et al., "Burden of valvular heart diseases: a population-based study," Lancet, vol. 368, Sep. 16, 2006, pp. 1005-1011.

Phelan, S., et al., "Epithelial displacement during breast needle core biopsy causes diagnostic difficulties in subsequent surgical excision specimens," Journal of Clinical Pathology, vol. 60, No. 4, Apr. 2007, pp. 373-376.

Podder, T. K., et al., "A novel curvilinear approach for prostate seed implantation," Journal of Medical Physics, vol. 39, No. 4, Apr. 2012, pp. 1887-1892.

Reed, K. B., et al., "Modeling and control of needles with torsional friction," IEEE Transactions on Biomedical Engineering, vol. 56, No. 12, Dec. 2009, pp. 2905-2916.

Roesthuis, R. J., et al., "Mechanics-based model for predicting in-plane needle deflection with multiple bends," 2012 4th IEEE RAS & EMBS International Conference on Biomedical Robotics and Biomechatronics, Roma, Italy, Jun. 24-27, 2012, pp. 69-74.

Ryu, S. C., "Optically Controlled Magnetic Resonance Imaging Compatible Active Needle," Dissertation submitted to the Department of Mechanical Engineering and the Committee on Graduate Studies of Stanford University in partial fulfillment of the requirements for the degree of Doctor of Philosophy, Dec. 2012, 127 pages.

Swensen, J. P., et al., "Torsional dynamics of steerable needles: Modeling and fluoroscopic guidance," IEEE Transactions on Biomedical Engineering, vol. 61, No. 11, Nov. 2014, pp. 2707-2717.

Van De Berg, N. J., et al., "Design Choices in Needle Steering—A Review," IEEE/ASME Transactions on Mechatronics, vol. 20, No. 5, Oct. 2015, pp. 2172-2183.

(56) References Cited

OTHER PUBLICATIONS

Volpe, A., et al., "Techniques, Safety and Accuracy of Sampling of Renal Tumors by Fine Needle Aspiration and Core Biopsy," The Journal of Urology, vol. 178, No. 2, Aug. 2007, pp. 379-386.

Youk, J. H., et al., "Analysis of false-negative results after US-guided 14-gauge core needle breast biopsy," European Radiology, vol. 20, No. 4, Oct. 28, 2009, pp. 782-789.

International Search Report and Written Opinion for International Patent Application No. PCT/US2018/025380, mailed Jun. 8, 2018, 12 pages.

Karimi, S. et al., "Self-sensing feedback control of multiple interacting shape memory alloy actuators in a 3D steerable active needle," Journal of Intelligent Material Systems and Structures, Jun. 3, 2020, Sage Journals, 17 pages.

Varnamkhasti, Z.K. et al., "Cable-Driven 3D Steerable Surgical Needle for Needle-Based Procedures," Proceedings of the 2020 Design of Medical Devices Conference (DMD2020), Apr. 6-9, 2020, Minneapolis, MN, USA, 5 pages.

Wellborn, P. et al., "Curving Clinical Biopsy Needles: Can We Steer Needles and Still Obtain Core Biopsy Samples?," Journal of Medical Devices, vol. 10, No. 3, Aug. 1, 2016, American Society of Mechanical Engineers, 2 pages.

Restriction Requirement for U.S. Appl. No. 16/077,394, mailed Nov. 14, 2019, 9 pages.

Non-Final Office Action for U.S. Appl. No. 16/077,394, mailed Feb. 24, 2020, 13 pages.

Notice of Allowance for U.S. Appl. No. 16/077,394, mailed Jun. 29, 2020, 9 pages.

\* cited by examiner

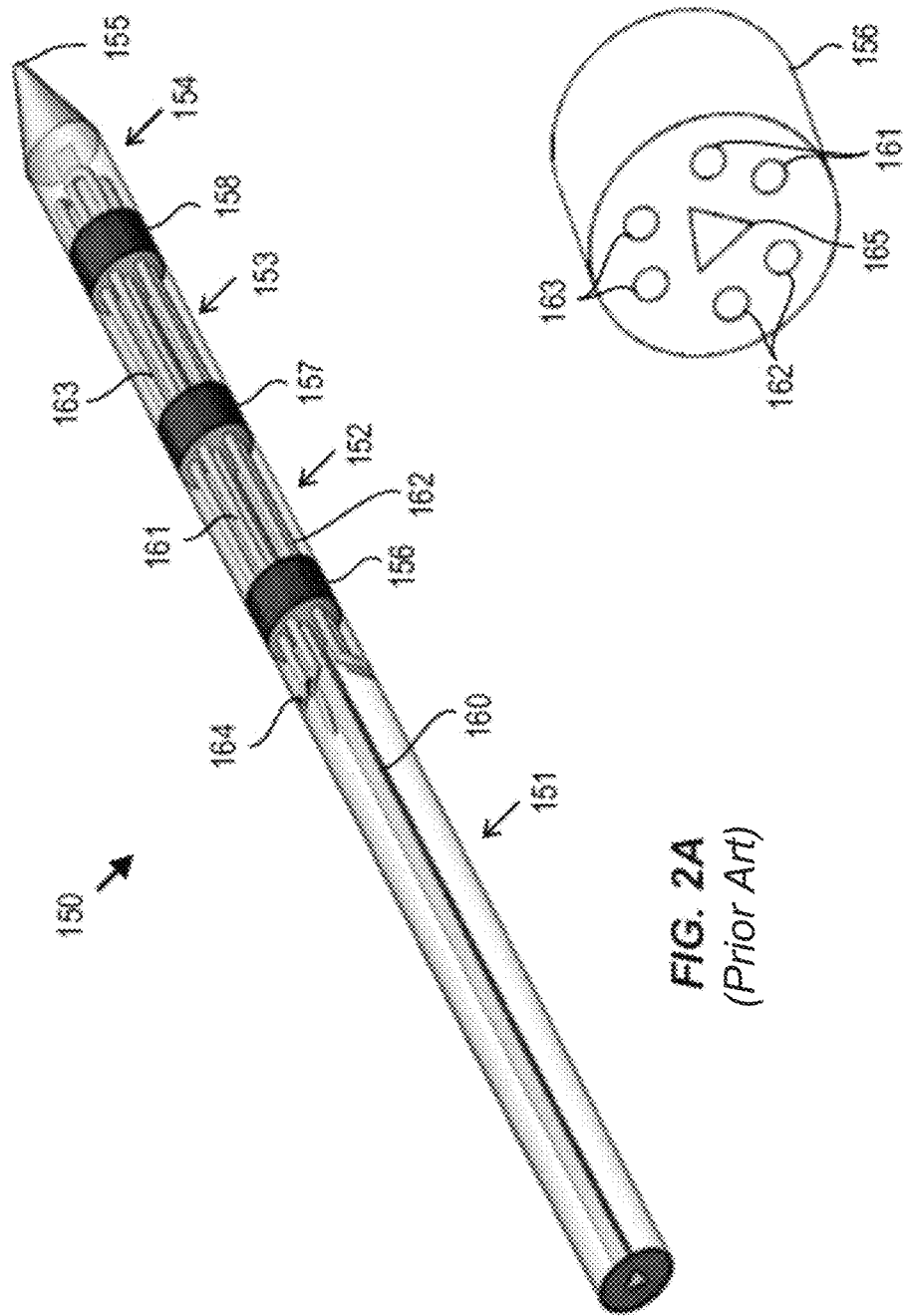
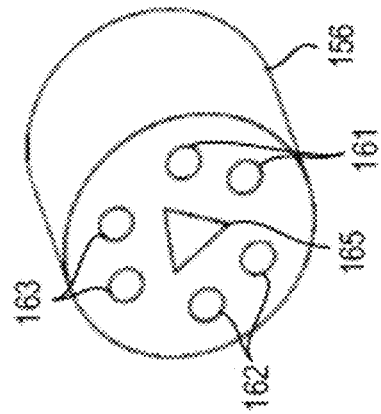
FIG. 2A (Prior Art)
FIG. 2B (Prior Art)

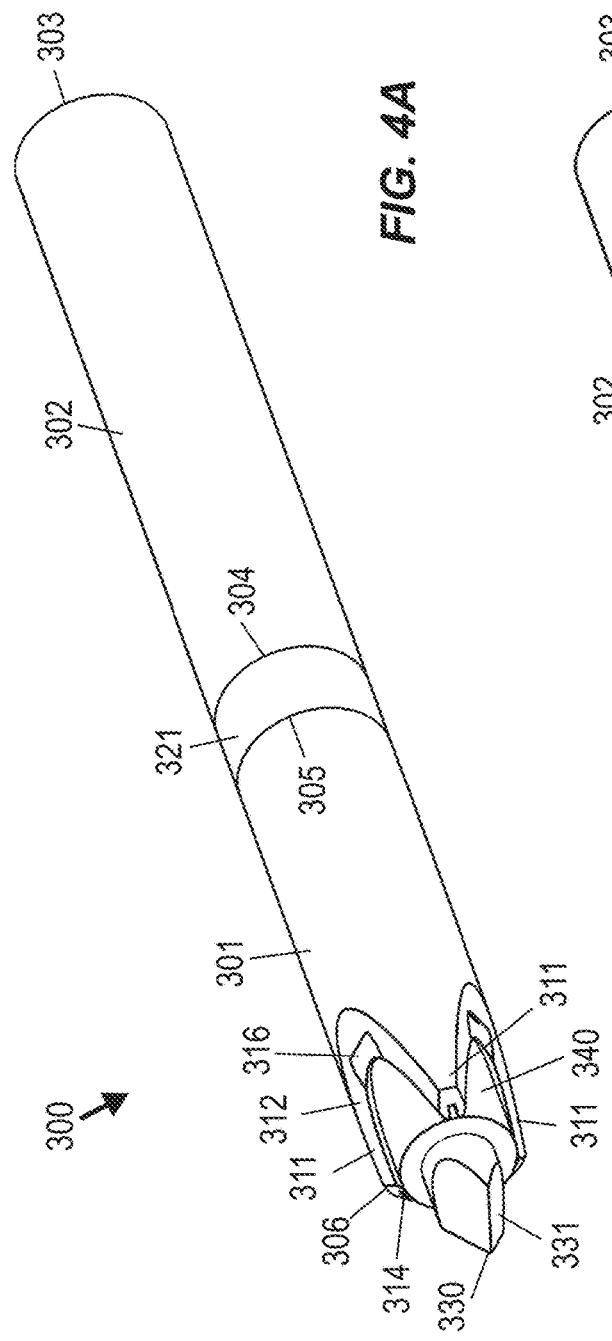
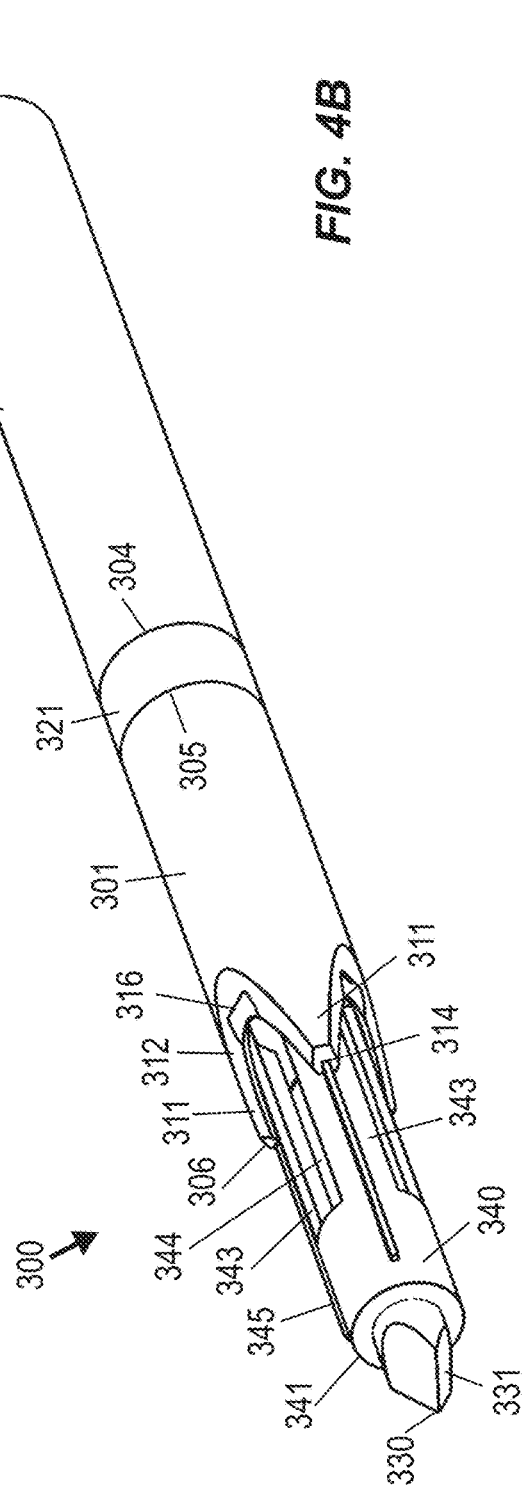
FIG. 4A
FIG. 4B

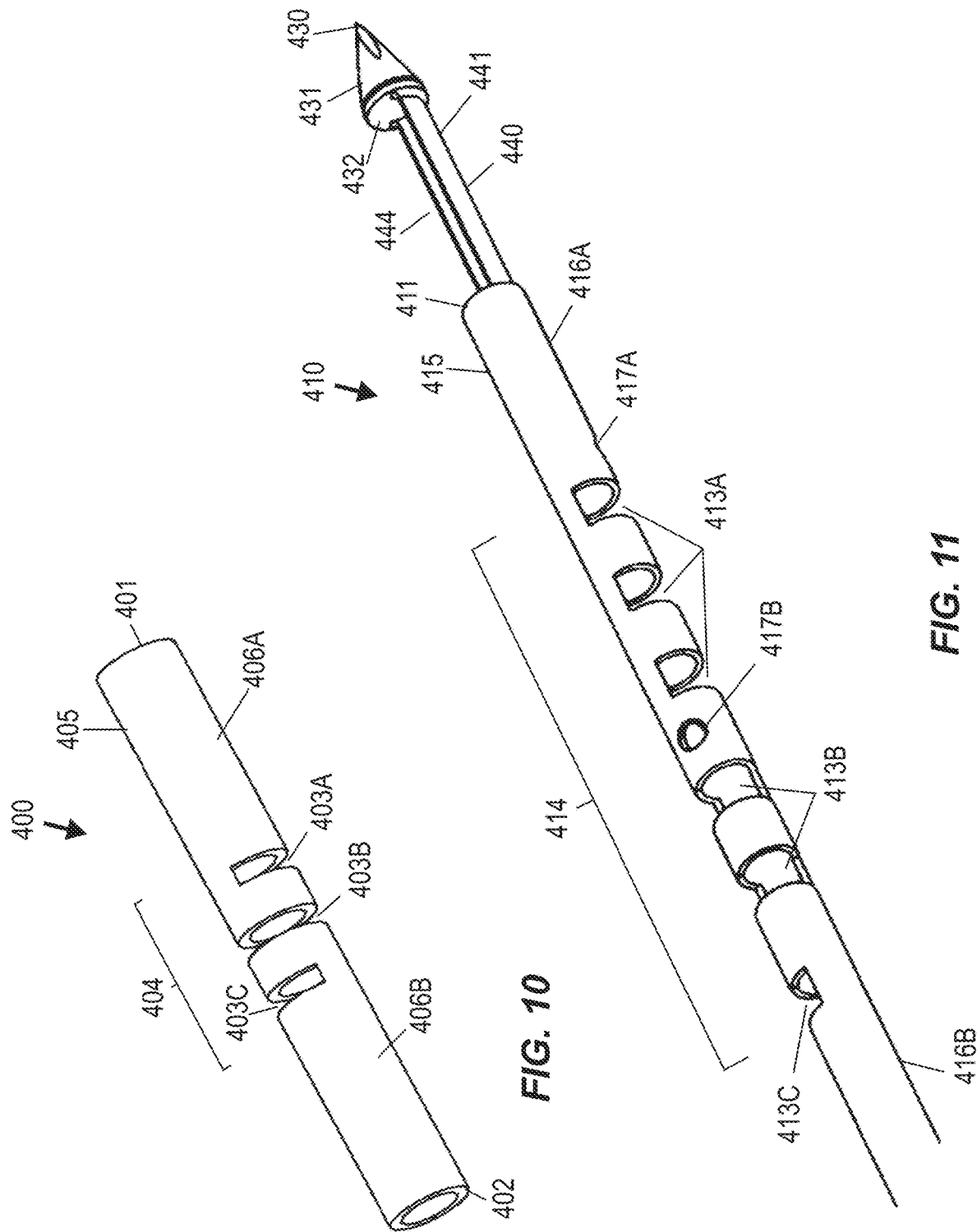

| Experiments | Unfiltered position data | | Filtered position data: outlier positions removed | |
| --- | --- | --- | --- | --- |
| | Average | Maximum | Average | Maximum |
| Liver 1 | 0.31 | 3.17 | 0.18 | 0.51 |
| Liver 2 | 0.62 | 5.08 | 0.19 | 0.42 |
| Liver 3 | 0.27 | 1.62 | 0.08 | 0.18 |
| Liver 4 | 0.74 | 7.36 | 0.48 | 0.73 |
| Liver 5 | 1.08 | 6.46 | 0.90 | 1.51 |

*FIG. 17D*

STEERABLE SURGICAL DEVICES, AND METHODS FOR THEIR USE AND TRACKING

CROSS-REFERENCE TO RELATED APPLICATION(S)

This application claims benefit of U.S. Provisional Patent Application No. 63/107,917 filed on Oct. 30, 2020, wherein the entire contents of the foregoing application are hereby incorporated by reference herein.

TECHNICAL FIELD

This invention relates to steerable surgical devices that are insertable in tissues of mammalian bodies, as well as methods for use and tracking of steerable surgical devices.

BACKGROUND

Surgical needles are commonly used in percutaneous diagnostic and therapeutic procedures. These procedures include tissue removal (biopsy), internal radiotherapy (brachytherapy), thermal ablations, and targeted drug delivery. The success of these procedures highly depends on the accuracy of needle placement at target locations. For example, malposition of the biopsy needle could result in a false diagnosis. Similarly, in brachytherapy, inaccurate positioning of the radioactive seeds could cause damage to the healthy tissue instead of attacking the cancerous cells. Precise delivery of therapeutic drugs to the diseased tissue or taking biopsy samples from suspicious tissue for diagnosis procedures is the most important factor governing the success of needle-based procedure. Conventionally, rigid passive needles (e.g., 17 or 18 gauge needles with 2.4 mm outer diameter and 1.8 mm inner diameter, suitable for passing radioactive seeds typically about 0.8 mm in diameter) are used in a straight path to reach the target. These needles would leave limited room for adjustment after their insertion into the patient's body. However, unpredicted factors such as human error, tissue deformation, and nonlinear and nonhomogeneous properties of the tissue undermines the placement accuracy.

As an alternative to rigid passive needles, flexible steerable needles have been proposed for enhanced navigation inside patient tissues. Passive bevel-tip needles beneficially utilize unbalanced forces on their tip to create a curved path inside the tissue and reach the target. This curved path could be used to maneuver around sensitive organs during surgical intervention. However, trajectory planning with passive needles is complicated and sometimes inaccurate. With passive needles, the deflection is basically governed by needle-tissue interactions. Passive needles with a predefined shape steer in two-dimensional (2D) space with a constant radius, and thereby require axial rotation to enable maneuvering and placement in 3D space. Rotation of a needle while the needle advances through tissue is not only difficult, but also increases the risk of tissue damage.

Active needles, on the other hand, can compensate for any possible misalignments via their actuation forces. Organ movements, physiological processes such as breathing, and human errors, are typical causes for these misalignments. With the help of the active needle's actuation and control, surgeons can guide their needle through a desired trajectory with increased accuracy. In certain cases, shape memory alloy (SMA) wire segments have been used to actuate needles within tissue. The silent and robust actuation of SMAs, their biocompatibility, and their high power-to-mass ratio make them attractive for development of active medical devices. A key feature of SMAs is their ability to undergo a large seemingly plastic strain and subsequently recover the strain through the application of heat or load removal. The actuation behavior of SMAs is generated when an internal crystalline transformation (e.g., between Austenite (high temperature) and Martensite (low temperature) phases) happens with application of load or heat. Actuation happens when the Martensite (enlarged shape) transforms to the Austenite phase (smaller or parent shape).

Certain steerable surgical devices incorporating multiple SMAs are disclosed in U.S. Pat. No. 10,806,898 to Konh, with the contents of such patent being incorporated by reference herein. An exemplary steerable surgical device includes a first tubular element, a second tubular element, a joint (e.g., at least a first joint), and a plurality of shape memory alloy wire elements. The first tubular element includes a first plurality of anchor points, and the second tubular element includes a second plurality of anchor points. The joint is arranged between the first tubular element and the second tubular element, and is configured to allow pivotal movement between the first tubular element and the second tubular element. The plurality of shape memory alloy wire elements extends across or through the first joint, is attached to the first plurality of anchor points, and is attached to the second plurality of anchor points. At least some shape memory alloy wire elements are independently actuatable to effectuate pivotal movement between the first tubular element and the second tubular element.

Other surgical procedures utilize elongated tubular bodies that are inserted into patients (e.g., for intravascular or other uses), with such tubular bodies being embodied in catheters, cannulas, guide wires, or the like.

Insertion of a narrow tubular body such as a flexible needle into a patient for performing a subcutaneous surgical procedure is a complex procedure for a physician. Typically, a surgeon will guide a needle to a target using an ultrasound image, which is susceptible to image noise, and it is frequently difficult to distinguish the needle from surrounding tissue unless there is precise alignment between the needle and an ultrasound probe. Moreover, mammalian (e.g., human) tissue is subject to deformation and movement. When a needle is inserted, tissue will be deformed and the target may move. When a needle is lost from a field of view of an imaging device, it can be challenging and time-consuming to re-establishing imaging of the needle, and/or further insertion of a needle may need to be stopped. Either of these factors can prolong the duration of a surgical procedure. Improved coordination between ultrasound imaging and needle movement, or elimination of a need for ultrasound imaging, would be welcome advances in the art.

It can also be challenging to combine the functions of steerability and tissue sample extraction capability in a single surgical device. Moreover, it may be difficult to extract multiple tissue samples from a patient without exerting undue trauma due to the need to remove and re-insert a surgical device multiple times.

The art continues to seek improvement in steerable surgical devices and methods for their use and tracking to enhance their utility.

SUMMARY

Disclosed herein by way of certain exemplary embodiments are steerable surgical devices each including tubular body members and at least one moveable joint, with a moveable tray member arranged to permit tissue extraction, augmented in certain embodiments with a retractable tip member. Further disclosed herein is a method for tracking position of a tip of a steerable surgical device that utilizes sensed electrical properties of shape memory alloy (SMA) elements and a sensed compressive force to identify force response of the SMA elements, that utilizes the force response and a joint deflection model of at least one joint to determine joint deflection, and that utilizes the determined joint deflection to map position of the tip in tissue, without requiring imaging. Additionally disclosed herein is a method for determining position of a tip of a steerable surgical device within tissue, utilizing transverse ultrasound probe images and utilizing image processing together with saved and predicted tip information. Further disclosed herein is a method for sequentially removing a plurality of samples from tissue utilizing a steerable surgical device, without requiring complete removal of the steerable surgical device from the tissue.

In one aspect, the disclosure relates to a steerable surgical device that comprises a tubular body, a plurality of tendon members, and a moveable tray member arranged to permit tissue extraction. The tubular body comprises a central longitudinal axis extending in a longitudinal direction, a base end, a distal end opposing the base end, a plurality of tubular body members including first and second tubular body members arranged between the base end and the distal end, and a first tubular joint member arranged between the first and second tubular body members, wherein the tubular body comprises a longitudinal passage extending through at least the plurality of tubular body members and the first tubular joint member. The plurality of tendon members extend from the at least the first tubular body member through the first tubular joint member to the second tubular body member, wherein tendon members of the plurality of tendon members are independently actuatable to effectuate pivotal movement between the first tubular body member and the second tubular body member. The moveable tray member is arranged at the distal end, the moveable tray member comprising at least one lateral opening and being configured to translate in the longitudinal direction between an extended position and a retracted position, wherein when the moveable tray member is in the extended position, the lateral opening is arranged to admit tissue into the longitudinal passage of the tubular body.

In certain embodiments, the steerable surgical device further comprises a retractable tip member arrangeable at a distal end of the moveable tray member, wherein the retractable tip member is configured to be retracted through the moveable tray member and the longitudinal passage to exit the tubular body, and is further configured to be returned through the longitudinal passage and the moveable tray member to be positioned at the distal end of the moveable tray member.

In certain embodiments, the retractable tip member has an associated guidewire extending in the longitudinal direction, to permit the retractable tip member to be retracted and returned by manipulation of the guidewire.

In certain embodiments, at the distal end, the first tubular body member comprises a plurality of longitudinally projecting portions separated by a plurality of spaces that are bordered by cutting surfaces of the first tubular body member, and the steerable surgical device is configured to permit a portion of the moveable tray member to extend in the longitudinal direction beyond the plurality of longitudinally projecting portions when the moveable tray member is in the extended position.

In certain embodiments, the at least one lateral opening of the moveable tray member comprises a plurality of lateral openings, with individual lateral openings of the plurality of lateral openings being registered with individual spaces of the plurality of spaces.

In certain embodiments, the plurality of tendon members comprises a plurality of shape memory alloy actuators.

In certain embodiments, the first tubular joint member comprises a hyperelastic material.

In certain embodiments, the first tubular joint member comprises a plurality of transverse slits extending substantially perpendicular to the longitudinal direction, and the plurality of transverse silts comprises at least one first transverse slit, at least one second transverse slit oriented differently from the at least one first transverse slit, and at least one third transverse slit oriented differently from each of the at least one first transverse slit and the at least one second transverse slit.

In certain embodiments, the plurality of tubular body members further comprises a third tubular body member; and the steerable surgical device further comprises a second tubular joint member arranged between the second tubular joint member and the third tubular joint member.

In certain embodiments, tendon members of the plurality of tendon members are distributed about the longitudinal axis at different angular positions; and the plurality of tendon members is anchored to a first group of anchor points arranged between the distal end and the first tubular joint member.

In certain embodiments, each tendon member of the plurality of tendon members is looped around a corresponding anchor point of the group of first anchor points, such that each tendon member includes continuous first and second segments extending in parallel in the longitudinal direction.

In another aspect, the disclosure relates to a steerable surgical device that comprises a tubular body defining a plurality of transverse slits that are oriented differently, multiple tendon members extending to anchor points positioned differently relative to the transverse slit, and a moveable tray member arranged to permit tissue extraction. The tubular body comprises a central longitudinal axis extending in a longitudinal direction, comprising a base end, comprising a distal end opposing the base end, and defines a plurality of transverse slits closer to the distal end than to the base end, the plurality of slits comprising at least one first transverse slit, at least one second transverse slit oriented differently from the at least one first transverse slit, and at least one third transverse slit oriented differently from each of the at least one first transverse slit and the at least one second transverse slit, the tubular body further comprising a longitudinal passage. A first anchor point is arranged between the at least one first transverse slit and the at least one second transverse slit, a second anchor point is arranged between the at least one second transverse slit and the at least one third transverse slit, and a third anchor point is arranged between the at least one third transverse slit and the distal end. A first tendon member extends from the first anchor point toward the base end, a second tendon member extends from the second anchor point toward the base end, and a third tendon member extends from the third anchor point toward the base end. A moveable tray member is arranged at the distal end, the moveable tray member comprising at least one lateral opening and being configured to translate in the longitudinal direction between an extended position and a retracted position. When the moveable tray member is in the extended position, the lateral opening is arranged to admit tissue for extraction through the longitudinal passage of the tubular body.

In certain embodiments, the tubular body consists of a unitary body member into which the at least one first transverse slit, the at least one second transverse slit, and at least one third transverse slit are defined.

In certain embodiments, the tubular body comprises a first body segment defining the at least one first transverse slit, a second body segment defining the at least one second transverse slit, and a third body segment defining the at least one third transverse slit.

In certain embodiments, the steerable surgical device further comprises a retractable tip member arrangeable at a distal end of the moveable tray member, wherein the retractable tip member is configured to be retracted through the moveable tray member and the longitudinal passage to exit the tubular body, and is further configured to be returned through the longitudinal passage and the moveable tray member to be positioned at the distal end of the moveable tray member.

In certain embodiments, the retractable tip member has an associated guidewire extending in the longitudinal direction, to permit the retractable tip member to be retracted and returned by manipulation of the guidewire.

In certain embodiments, at the distal end, the first tubular body member comprises a plurality of longitudinally projecting portions separated by a plurality of spaces that are bordered by cutting surfaces of the first tubular body member; and the steerable surgical device is configured to permit a portion of the moveable tray member to extend in the longitudinal direction beyond the plurality of longitudinally projecting portions when the moveable tray member is in the extended position.

In certain embodiments, the at least one lateral opening of the moveable tray member comprises a plurality of lateral openings, with individual lateral openings of the plurality of lateral openings being registered with individual spaces of the plurality of spaces.

In certain embodiments, the plurality of tendon members comprises a plurality of shape memory alloy actuators.

In certain embodiments, tendon members of the plurality of tendon members are distributed about the longitudinal axis at different angular positions; and the plurality of tendon members is anchored to a first group of anchor points arranged between the distal end and the first tubular joint member.

In certain embodiments, each tendon member of the plurality of tendon members is looped around a corresponding anchor point of the group of first anchor points, with each tendon member including continuous first and second segments extending in parallel in the longitudinal direction.

In another aspect, the disclosure relates to a method for tracking position of a tip of a steerable surgical device comprising a base end, a distal end, an elongated body structure including at least one tubular joint member arranged between corresponding ones of a plurality of tubular body members, and including multiple longitudinally oriented shape memory alloy elements arranged in or on the elongated body structure when the elongated body structure is inserted into tissue. The method comprises: sensing electrical properties of the multiple longitudinally oriented shape memory alloy elements; sensing compressive force at the base end; utilizing (i) the sensed electrical properties and (ii) the sensed compressive force to identify force response of the shape memory alloy elements; utilizing the identified force response of the shape memory alloy elements, and utilizing a predetermined joint deflection model of the tubular joint member, to determine deflection of the at least one tubular joint member; and utilizing the determined deflection of the at least one tubular joint member to map position of the tip of the surgical steerable instrument within the tissue.

In certain embodiments, the method further comprises sensing at least one of (a) rotation of the steerable surgical device and (b) insertion length of the steerable surgical device to produce sensed information, and further utilizing the sensed information in the mapping of position of the tip of the surgical steerable instrument within the tissue.

In certain embodiments, the at least one tubular joint member comprises a hyperelastic material.

In certain embodiments, the at least one tubular joint member comprises a plurality of transverse slits that comprises at least one first transverse slit, at least one second transverse slit oriented differently from the at least one first transverse slit, and at least one third transverse slit oriented differently from each of the at least one first transverse slit and the at least one second transverse slit.

In certain embodiments, the longitudinally oriented shape memory alloy elements comprise shape memory alloy actuators that are independently actuatable to effectuate pivotal movement between corresponding ones of the plurality of tubular body members.

In another aspect, the disclosure relates to a method for determining position of a tip of a steerable surgical device within tissue, the steerable surgical device comprising an elongated body structure and a tip, the method comprising: positioning an ultrasound probe to capture images transverse to the elongated body structure; moving the ultrasound probe substantially concurrently with movement of the steerable surgical device; processing images obtained from the ultrasound probe to determine presence and position of the tip in the images; and adjusting relative speed between ultrasound probe movement and steerable surgical device movement, responsive to a determination from the image processing that the tip is not present in one or more images captured by the ultrasound probe.

In certain embodiments, wherein the adjusting of relative speed comprises reducing speed of movement of ultrasound probe and/or increasing speed of movement of the steerable surgical device.

In certain embodiments, the method further comprises saving information indicative of tip position responsive to the image processing.

In certain embodiments, the saved information indicative of tip position comprises detected tip position if the tip is determined to be present in a processed image.

In certain embodiments, the saved information indicative of tip position comprises a previously detected tip position if the tip is not determined to be present in a processed image.

In certain embodiments, the saved information indicative of tip position comprises a predicted tip position if the tip is not determined to be present in a processed image.

In certain embodiments, the predicted tip position comprises a position determined by extrapolation of multiple prior tip positions.

In certain embodiments, the movement of the ultrasound probe is automated in relation to movement of the steerable surgical device.

In another aspect, the disclosure relates to a method for removing a plurality of samples from tissue utilizing a steerable surgical device that includes (i) a tubular body comprising a central longitudinal axis extending in a longitudinal direction, a base end, a distal end opposing the base end, a plurality of tubular body members including first and second tubular body members arranged between the base end and the distal end, and a first tubular joint member arranged between the first and second tubular body members, wherein the tubular body comprises a longitudinal passage extending through at least the plurality of tubular body members and the first tubular joint member, (ii) a plurality of tendon members that are independently actuatable to effectuate pivotal movement between the first tubular body member and the second tubular body member, (iii) a moveable tray member arranged at the distal end, the moveable tray member comprising at least one lateral opening in communication with the longitudinal passage and being configured to translate in the longitudinal direction between an extended position and a retracted position, and (iv) a retractable tip member arrangeable at a distal end of the moveable tray member. The method comprises: inserting a portion of the steerable surgical device into the tissue to arrange moveable tray member at a first position in the tissue; extending the retractable tip member to an extended state to position the moveable tray member at a first position in the tissue; while the moveable tray member is positioned at the first position, drawing a first tissue sample through at least one lateral opening into the longitudinal passage; withdrawing the tip member through the longitudinal passage to extract the first tissue sample from the base end of the steerable surgical device, while the portion of the steerable surgical device remains in the tissue; returning the tip member through the longitudinal passage to contact the moveable tray member; moving the steerable surgical device to a second position in the tissue without completely removing the steerable surgical device from the tissue; while the moveable tray member is positioned at the second position, drawing a second tissue sample through the at least one lateral opening into the longitudinal passage; and withdrawing the tip member through the longitudinal passage to extract the second tissue sample from the base end of the steerable surgical device.

In another aspect, any one or more aspects or features described herein may be combined with any one or more other aspects or features for additional advantage.

Other aspects and embodiments will be apparent from the detailed description and accompanying drawings.

Those skilled in the art will appreciate the scope of the present disclosure and realize additional aspects thereof after reading the following detailed description of the certain exemplary embodiments in association with the accompanying drawing figures.

BRIEF DESCRIPTION OF DRAWINGS

FIG. 2A is a perspective view of a modeled active needle including first through fourth tubular body members with soft elastic joints arranged between different body member, with through-holes defined through the body members and joints to permit passage of shape memory alloy wire actuators.

FIG. 2B is a perspective view of one of the elastic joints of FIG. 2A.

FIG. 4A is a perspective view of at least a portion of a steerable surgical device suitable for extraction of at least one tissue sample according to one embodiment, the device having tubular body members, a joint member, a moveable tray member, and a retractable tip member, with the moveable tray member in a retracted state.

FIG. 4B is a perspective view of the at least a portion of a steerable surgical device of FIG. 4A, with the moveable tray member in an extended (or deployed) state.

FIG. 10 is a perspective view of a tubular body defining differently oriented first, second, and third transverse slits, with the tubular body being useable in a steerable surgical element according to certain embodiments.

FIG. 11 is a perspective view of a portion of a steerable surgical device defining differently oriented first, second, and third transverse slits, with a moveable tray member in an extended (or deployed) state.

FIG. 17D is a table providing distance error between needle tip positions found by three-dimensional needle shape prediction steps disclosed herein and a robot-assisted ultrasound tracking steps disclosed herein, for manipulation of a steerable surgical needle according to five needle insertion tests in ex vivo beef liver tissue.

DETAILED DESCRIPTION

Figure 1A:
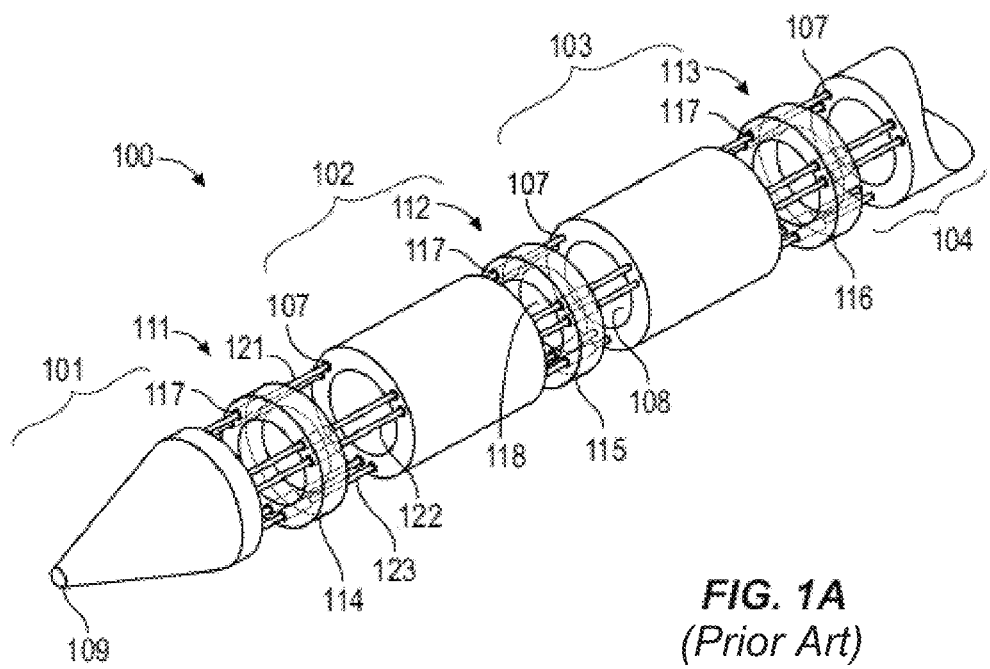
FIG. 1A is an exploded perspective view of a known steerable surgical device including shape memory alloy wire elements extending through longitudinal bores defined in tubular elements and joint elements of the steerable surgical device, to provide an introduction to various elements of steerable surgical devices described hereinafter.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

Aspects of the disclosure may be understood following introduction of steerable surgical devices incorporating multiple shape memory alloy actuators. A steerable surgical device may include a flexible joint positioned between first and second tubular elements, with multiple shape memory alloy wire elements extending across or through the joint being independently actuatable to effectuate pivotal movement between the first and second tubular elements along multiple non-parallel planes. A shape memory alloy is an alloy that "remembers" an original state and that, following deformation, returns to its pre-deformed state when actuated (e.g., electric current, heat, magnetic field, etc.). In certain embodiments, multiple (e.g., two, three, or more) shape memory alloy wire elements are attached to circumferentially-spaced first anchor points of the first tubular element and circumferentially-spaced second anchor points of the second tubular element, and are independently actuatable to effectuate pivotal movement between the first and second tubular elements. The shape memory alloy wire elements predictably and reliably contract relative to the current transmitted therethrough. In this way, the steerable surgical device provides for precise multi-dimensional pivotal movement of the first tubular element relative to the second tubular element. For example, the presence of at least three properly configured and independently actuatable shape memory alloy wire elements may permit adjustment of pivot angles between the first tubular element and the second tubular element along at least three non-parallel planes. This exacting control and precision allow the steerable surgical device to be fed through and/or inserted into tissue of a mammalian subject for a variety of medical applications. It is to be appreciated that additional joints and tubular body elements may be provided.

Figure 1B:
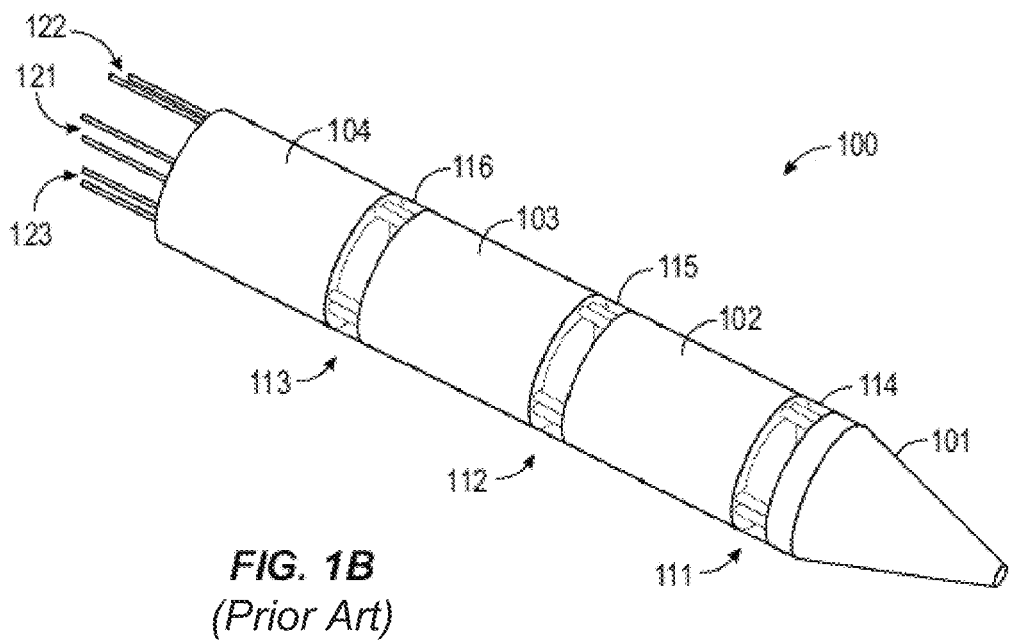
FIG. 1B is a perspective view of the steerable surgical device of FIG. 1A in an assembled state.

An exemplary steerable surgical device is illustrated in FIGS. 1A and 1B, with such figures being excerpted from U.S. Pat. No. 10,806,898. FIG. 1A is an exploded perspective view of a steerable surgical device 100 including shape memory alloy wire elements 121-123 extending through longitudinal bores 107 defined in at least some tubular elements 102-104, and extending through longitudinal bores 117 defined in flexible elements 114-116 of the steerable surgical device 100. The steerable surgical device 100 includes first through fourth tubular elements 101-104, with the first tubular element including a needle tip 109 and having a substantially conical shape. Each flexible element 114-116 is positioned between, and forms a joint 111-113 between, a different pair of tubular elements 101-104. Tubular elements 102-104 may include an interior cavity 108, and each flexible element 114-116 likewise may include an interior cavity 118, such that the foregoing items 102-104, 114-116 may each be substantially annular in shape, and collectively define a longitudinal passage. As shown in FIG. 1A, the tubular elements 102-104 each include three closely-spaced pairs of longitudinal bores 107, with a center of each pair of longitudinal bores 107 being about 120 degrees apart from a center of each other pair of longitudinal bores 107. Likewise, the flexible elements 114-116 each include three closely-spaced pairs of longitudinal bores 117, with a center of each pair of longitudinal bores 117 being about 120 degrees apart from a center of each other pair of longitudinal bores 117 defined through the flexible elements 114-116. The respective bores 107, 117 defined in the tubular elements 102-104 and defined in the flexible elements 114-116 are configured to permit the passage of shape memory alloy wire elements 121-123. Providing shape memory alloy wire actuators completely enclosed inside the steerable surgical device 100 (e.g., within bores 107, 117 defined in the tubular elements 102-104 and defined in the flexible elements 114-116) avoids contact between the shape memory alloy wire actuators and tissue, thereby preventing the heating of shape memory alloy actuators from causing tissue damage when the steerable surgical device 100 is used inside a patient's body.

In certain embodiments, a first end of each shape memory alloy wire element 121-123 may be inserted (in a direction generally toward the needle tip 109) through a longitudinal bore 107 defined in the fourth tubular element 104, through a longitudinal bore 117 defined in the third flexible element 116, through a longitudinal bore 107 defined in the third tubular element 103, through a longitudinal bore 117 defined in the second flexible element 115, through a longitudinal bore 107 defined in the second tubular element 102, through a longitudinal bore 117 defined in the first flexible element 114, and into an interior of the first tubular element 101 to be received by an anchor (e.g., loop, post, or the like), and then returned in reverse order (away from the needle tip 109) through a paired (closely spaced) longitudinal bore 117 defined in the first flexible element 114, through a paired (closely spaced) longitudinal bore 107 defined in the second tubular element 102, and so on, until the respective shape memory alloy wire element 121-123 exits the fourth tubular element 104. In this manner, each pair of longitudinal bores 107 in the tubular elements 102-104 and each pair of longitudinal bores 117 in the flexible elements 114-116 receives a single shape memory wire element 121-123, such that first and second ends of each shape memory wire element 121-123 may be accessible at an end of the steerable surgical device 100 distal from the needle tip 109 (i.e., as shown in FIG. 1B). Actuation of a single shape memory wire element 121-123 may cause each joint 111-113 to pivot along one deflection plane. Individually controllable actuation of the shape memory wire elements 121-113 may permit the pivotal movement of the needle tip 109 along at least three planes, such that three-dimensional pivotal movement of the needle tip 109 is enabled.

FIG. 1B is a perspective view of the steerable surgical device 100 of FIG. 1A in an assembled state, showing the flexible elements 111-113 arranged between and in contact with different pairs of the tubular elements 101-104, and showing both ends of each of three shape memory alloy wire elements 121-123 extending outward beyond the fourth tubular element 104.

Elements of the steerable surgical device 100 of FIGS. 1A and 1B may be produced by any suitable means, including extrusion, 3D printing, or the like. In certain embodiments, the tubular elements 101-104 may comprise polymeric material (optionally reinforced) such as fluoropolymers, polyolefins, polyamides, or the like.

The foregoing steerable surgical device 100 with clinically feasible size is insertable into tissue of a mammalian body, and is capable of 1D manipulation and control to reach a target location via robotic instruments (e.g., utilizing at least one processor configured to execute machine-readable instructions embodied in software, firmware, or a combination thereof). In certain embodiments, the at least one processor may be embodied in one or more computing devices.

The unique characteristics of SMAs known as Shape Memory Effect (SME) and pseudo-elasticity (PE), along with desirable material properties such as corrosion resistance and biocompatibility, plus their high actuation energy densities, have made SMAs a suitable choice for use in actuating active needles. Various heating and cooling techniques to drive SMAs include electrical heating (Joule heating) or inductive heating, air cooling, forced air/liquid cooling, etc. Another distinct advantage of SMAs as actuators is their self-sensing capabilities. Along with strain recovery, the electrical resistance of a SMA actuator alters notably during the transformation between austenite to martensite or vice-versa. This phenomenon can be applied to design a feedback positioning control by measuring electrical resistance variation through SMA actuators to estimate the actuation strain. Due to the correlation between the actuation strain and the electrical resistance (which may be determined quantitatively through characterization experiments), SMAs can be used as smart actuators.

Another steerable surgical device in the form of a prototype SMA multi-wire actuated 3D steerable active needle is shown in FIG. 2A. The prototype was a 4:1 scaled model of 17-gauge hypodermic needle (outer diameter of 6 mm, inner diameter of 1.5 mm) fabricated of 3D printed parts (namely, a rigid base and links, and soft joints) and was used to evaluate precision of a self-sensing electrical resistance feedback control scheme. FIG. 2A is a perspective view of the modeled active needle 150, including first through fourth tubular body members 151-154 (with the fourth body member 154 having a pointed tip), and soft elastic joints 156-158 arranged between different body members 151-154. A longitudinal alignment member 160 extends through triangular central apertures defined in the body members 151-154 and the joints 156-158, to facilitate concentric alignment of the foregoing components. Three equi-angularly distanced pairs of through-holes 161-163 extend through the body members 151-154 and the joints 156-158 to accommodate the passage of three SMA-wire actuators (not shown), which extend through lateral openings 164 in the first tubular body member 151, pass through the body members 151-154 in a generally longitudinal direction, and loop through an internal structure of the needle 150 (e.g., to reverse direction within the fourth body member 154). The configuration of the needle 150 was designed to achieve active 3D steering, with the soft elastic joints 156-158 serving to enhance flexibility of the needle 150. Actuation of three SMA-wire actuators extending through the paired through-holes 161-163 may be used to realize 3D motion at a tip 155 of the needle 150. FIG. 2B is a perspective view of one of the elastic joints 156 separate from the needle 150, showing the paired through-holes 161-163 as well as a triangular central aperture 165 extending therethrough. The soft elastic joints 156-158 are fabricated of PROTOLABS® Digital Clear/Translucent Photopolymer material having a Shore A hardness value of 60, a tensile strength of 4.5 MPa, and 170% elongation at breakage. The body members 151-154 are fabricated with Somos® PerForm polymeric material having a tensile strength of 68 MPa.

Figure 3:
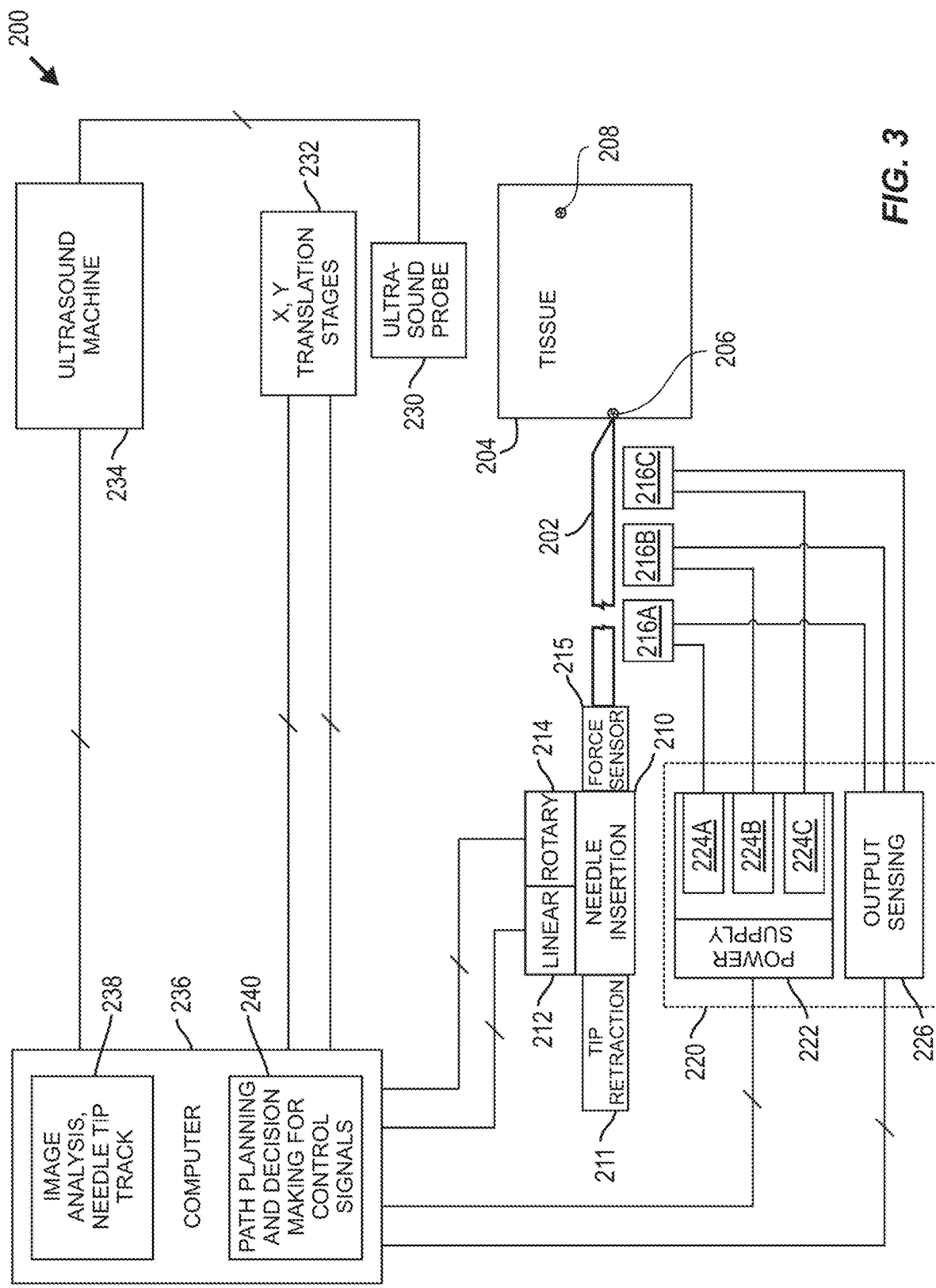
FIG. 3 is a schematic diagram showing interconnections between various elements of a system for controlling and tracking movement of a steerable surgical device that is insertable into tissue of a mammalian body according to one embodiment of the present disclosure.

FIG. 3 is a schematic diagram showing interconnections between various elements of a system 200 for controlling movement of a steerable surgical device 202 that is configured to be inserted into tissue 204 of a mammalian body, according to one embodiment of the present disclosure. The tissue 204 is shown at lower right, with an insertion point 206 and a target point 208 (which is internal to the tissue 204) marked therein. Just outside the tissue 204 proximate to the insertion point 206, a steerable surgical device (e.g., including or consisting of a needle) 202 is coupled with a needle insertion apparatus 210 that includes a first motor 212 for controlling linear insertion of the steerable surgical device 202, and a second motor 214 for controlling rotary position of the steerable surgical device 202. A force sensor 215 (e.g., for sensing compressive force) may be positioned proximate to a base of the steerable surgical device 202. A tip retraction mechanism 211 may be provided to selectively retract and advance a guidewire (not shown) associated with a retractable tip member and/or a moveable tray member (e.g., shown in FIGS. 5A-5C and 6B-6C) of the steerable surgical device 202. Further illustrated are three SMA actuators 216A-216C (that may each embody a NiTi wire) coupled to a direct current (DC) programmable power supply 220 including a power supply module 222 and an output sensing module 226. Each SMA actuator 216A-216C is coupled to a different gain (output) 224A-224C of the power supply module 222 for independent control of the supply of electric current to the shape memory alloy actuators 216A-216C. The output sensing module 226 is used to measure voltage and current flowing through each SMA actuator 216A-216C. It is to be appreciated that the shape memory alloy actuators 216A-216C may be arranged at different angular positions relative to the steerable surgical device 202 (e.g., generally one hundred twenty degrees apart such as shown in FIGS. 1 and 2). The SMA actuators 216A-216C are configured to effectuate pivotal movement between tubular elements (not shown) of the steerable surgical device 202 responsive to application of electric current to the SMA actuators 216A-216C. An ultrasound probe 230 is arranged proximate to the tissue 204, with associated x and/or y translation stages 232 arranged to permit the ultrasound probe 230 to move relative to the tissue 204. The ultrasound probe 230 is coupled to an ultrasound imaging machine 234 (e.g., an Chison ECO5 ultrasound machine in certain embodiments). A computer 236 (e.g., incorporating at least one processor) is coupled with the above-mentioned components. As noted, the computer 236 provides multiple functions, wherein specific functions may be provided by modules such as an image analysis and needle tip tracking module 238 (utilizing images received from the ultrasound machine 224) and a path planning and decision making module 240 that may generate control signals. The computer 236 provides command signals to drive the first and second motors 212, 214, as well as the shape memory alloy actuators 216A-216C (by way of the power supply module 222 with dedicated current gains 224A-224C) to effectuate movement of the steerable surgical device 202 in the tissue 204 with steering along a path between the insertion point 206 and the target point 208. Such path may include one or more curves, bends, and/or twists, and the steerable surgical device 202 may be actuated to change its shape (e.g., curvature) during transit with the tissue 204. Signals indicative of or derived from voltage and/or current flowing through the shape memory alloy actuators 216A-216C, and further derived from the force sensor 215, are supplied from the output sensing module 226 to the computer 236. The computer 236 also provides command signals to the x and/or y translation stages 232 to move the ultrasound probe 230 relative to the tissue 204.

In certain embodiments, a steerable surgical device is suitable for extraction of at least one tissue sample from tissue into which the device is inserted. In certain embodiments, a moveable tray member is positioned proximate to a distal end of a tubular body structure of a steerable surgical device, wherein the moveable tray member may be moved (e.g., translated in a longitudinal direction) between an extended (or deployed state) and a retracted state. In an extended state, the moveable tray member may be moved forward relative to a distal end of the tubular body structure, wherein such movement may be caused by advancement of an internal guidewire that is either coupled directly to the moveable tray member, or is coupled to a retractable tip member that is configured to engage and cooperate with the moveable tray member. A moveable tray member may fit within an interior portion of a tubular body member. The moveable tray member may include at least one lateral opening that permits ingress of tissue when the retractable tip member is an extended or deployed state, for extraction of tissue through a longitudinal passage defined in the tubular body structure. In certain embodiments, one or more cutting surfaces may be associated with the body structure and/or the moveable tray member, to aid in separating a tissue sample from surrounding tissue when the moveable tray member is moved from the extended (or deployed) state to the retracted state, wherein movement of the moveable tray member to the retracted state pulls a tissue sample into the longitudinal passage of the tubular body structure. In certain embodiments, a tissue sample is retained in the longitudinal passage and may be extracted after a steerable surgical device is removed from tissue. In other embodiments, a tissue sample may be removed from the longitudinal passage (and extracted from a base of the surgical device) while the steerable surgical device remains positioned in the tissue, by pulling a guidewire associated with a retractable tip member, to cause the retractable tip member transmit from the distal end of the tubular body structure to a proximal end of the tubular body structure, wherein such movement causes a captured tissue sample to also be extracted through the longitudinal passage. After the retractable tip member is moved to such a retracted state to permit tissue sample removal, the retractable tip member may be returned to the distal end of the tubular body structure to be coupled with the moveable tray member, wherein such movement may be caused by pushing on the guidewire associated with the retractable tip member. Multiple tissue samples may be sequentially extracted from bulk tissue without removal of the steerable surgical device from tissue according to such a method, suitable for performing procedures such as lumpectomy without undue trauma that would be entailed if the entire surgical device needed to be removed and reinserted for extraction of each tissue sample. In certain embodiments, a tubular body member includes a plurality of longitudinally projecting portions separated by a plurality of spaces that are bordered by cutting surfaces of the first tubular body member. In such an embodiment, the moveable tray member may include multiple lateral openings, with individual lateral openings being registered with individual spaces. Movement of the moveable tray member to the extended position may cause a portion of the moveable tray member to extend in the longitudinal direction beyond the longitudinally projecting portions to permit ingress of tissue through one or more of the lateral openings. In certain embodiments, an inner surface of a tubular body member may include multiple longitudinal slots configured to receive longitudinal rails projecting from an outer surface of a moveable tray member, to guide and limit movement of the moveable tray member in the longitudinal direction.

FIGS. 4A and 4B provide perspective views of at least a portion of a steerable surgical device 300 suitable for extraction of at least one tissue sample according to one embodiment, the steerable surgical device 300 having tubular body members 301, 302, a joint member 321, a moveable tray member 340, and a retractable tip member 330, with FIG. 4A showing the moveable tray member 340 in an extended state, and with FIG. 4B showing the moveable tray member 340 in a retracted state. The joint member 321 is positioned between a proximal end 305 of the first tubular body member 301 and a distal end 304 of the second tubular body member 302. In certain embodiments, the tubular body members 301, 302 may comprise semi-rigid or soft materials that may be formed of 3D printed parts. In certain embodiments, the joint member 321 may comprise a hyperelastic material (e.g., a highly elastic material characterized by a non-linear stress-stretch response). In other embodiments, the joint member 321 may comprise a plurality of transverse slots oriented in different directions to confer flexibility. The tubular body members 301, 302 and the joint member 321 in combination form a tubular body structure extending from a proximal end 303 to a distal end 306. It is to be appreciated that although a relatively short second tubular body member 302 is shown, an operative steerable surgical device may include a second tubular body member 302 that is significantly longer than illustrated. The first tubular body member 301 includes first to third longitudinally projecting portions 311 at the distal end 306, with cutting surfaces 312 at surfaces bounding gaps 313 between the longitudinally projecting portions 311. Anchoring points 316 for receiving internal tendons (e.g., SMA actuating tendons, or metal wires to be mechanically tensioned) are additionally provided at portions of the first tubular body structure 301 between the longitudinally projecting portions 311. Longitudinal slots 314 are further defined by the longitudinally projecting portions 311, to receive longitudinal rails 345 of the moveable tray member 340. A tip member 330 having blade surfaces 331 is positioned at a distal end 341 of the moveable tray member 340. The tip member 303 may comprise surgical grade steel or ceramic materials, while the moveable tray member 340 may comprise a superelastic Nitinol material having selected surfaces thereof sharpened and slotted by machining tools. As shown in FIG. 4B, when the moveable tray member 340 is arranged in an extended state (with translational movement guided and limited by cooperation of the longitudinal rails 345 with the longitudinal slots 314), lateral openings 344 of the moveable tray member 340 defined between tray body portions 343 are exposed (and registered with gaps between projecting portions 311 of the first tubular body member 301) to permit ingress of tissue. When the retractable tip member 340 is pulled (e.g., using an internal guidewire, (not shown)) toward the distal end 303, cutting surfaces 312 bordering gaps between the projecting portions 311 facilitate separation (from bulk tissue) of a sample of tissue received by the lateral openings 344 to an interior of the moveable tray member 340, to permit a tissue sample (e.g., about 2 cm long) to be received into a longitudinal passage of the tubular body members 301, 302. The above-mentioned internal guidewire may be coupled to the retractable tip member 330, wherein movement of the guidewire combined with coupling between the retractable tip member 330 and the moveable tray member 340 may also cause translational movement of the moveable tray member 340. However, cooperation between the longitudinal rails 345 and the longitudinal slots 314 limits the range of travel (and limits rotation) of the moveable tray member 340, such that forward (or distal) movement of the tip member 330 is restrained by the moveable tray member 340, but the tip member 330 is permitted to disengage from the moveable tray member 340 and move through a longitudinal passage defined by the tubular body members 301, 302 (and the joint member 321) when the guidewire is pulled in a rearward or proximal direction.

In certain embodiments, an electromagnetic (EM) sensor may be placed at or along the tip member 340 to facilitate position tracking during insertion of the steerable surgical device, wherein this sensor may be removed during excision of one or more tissue samples.

Figure 5A:
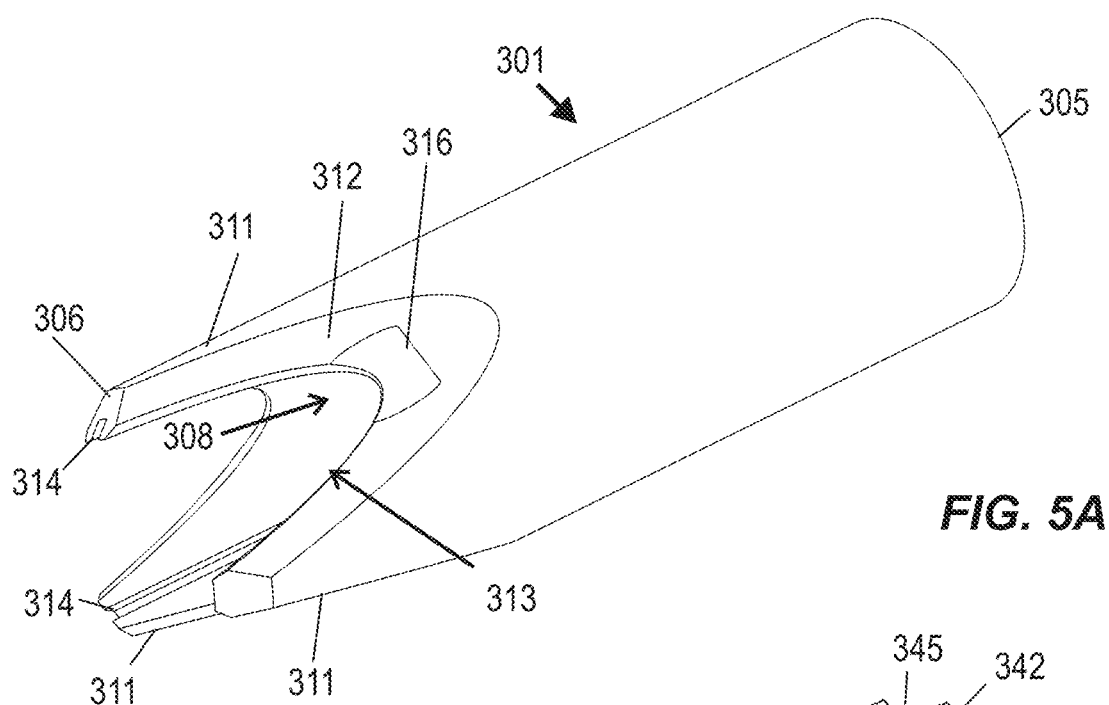
FIG. 5A is a perspective view of a first tubular body member of the steerable surgical device of FIGS. 4A-4B, including three longitudinally projecting portions.

FIG. 5A is a perspective view of the first tubular body member 301 of the steerable surgical device 300 of FIGS. 4A-4B. As shown, three longitudinally projecting portions 311 are arranged at the distal end 306, which opposes the proximal end 305. The longitudinally projecting portions 311 are separated by gaps 313, which are bounded by cutting surfaces 312. Anchoring points 316 for receiving internal tendons (not shown) are provided between the longitudinally projecting portions 311, wherein such tendons may be arranged internal to a wall of the tubular body member 301. Each longitudinally projecting portion 311 defines a longitudinal slot 314 along an internal surface thereof, with the tubular body member 301 and the longitudinally projecting portions 311 surrounding a longitudinal passage 308.

Figure 5B:
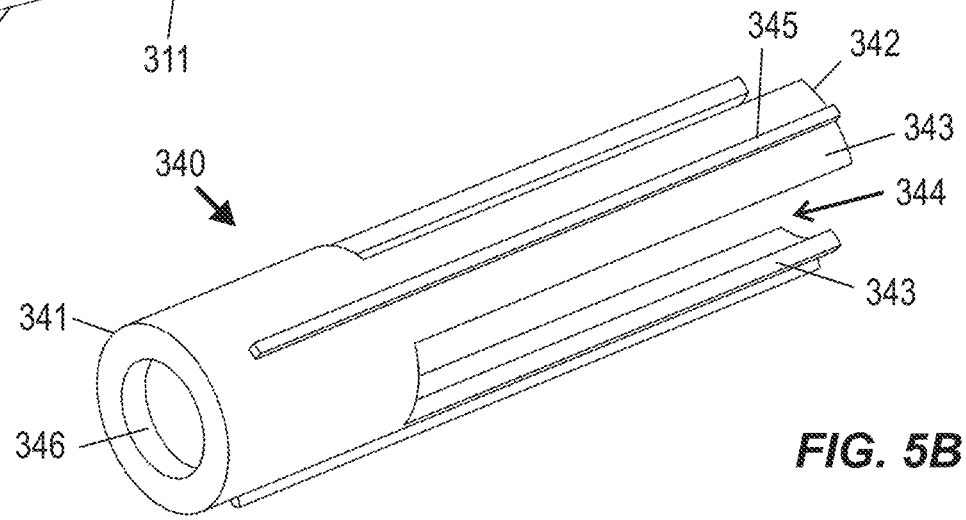
FIG. 5B is a perspective view of the moveable tray member of the steerable surgical device of FIGS. 4A-4B.

FIG. 5B is a perspective view of the moveable tray member 340 of the steerable surgical device 300 of FIGS. 4A-4B. As shown, the moveable tray member includes a distal end 341 defining a central aperture 346 (for receiving the tip member 330 shown in FIGS. 4A-4B), and a proximal end 342 where three tray body portions 343 terminate. Each tray body portion 343 includes a longitudinal rail 345, wherein one or more tray body portions 343 may include a longitudinal rail of a different (e.g., shorter) length than the others, to cooperate with a corresponding longitudinal slot of reduced length defined in the first body member 301 (of FIGS. 4A-4B) to limit longitudinal travel of the moveable tray member 340. Lateral openings 344 are provided between corresponding pairs of tray body portions 343.

Figure 5C:
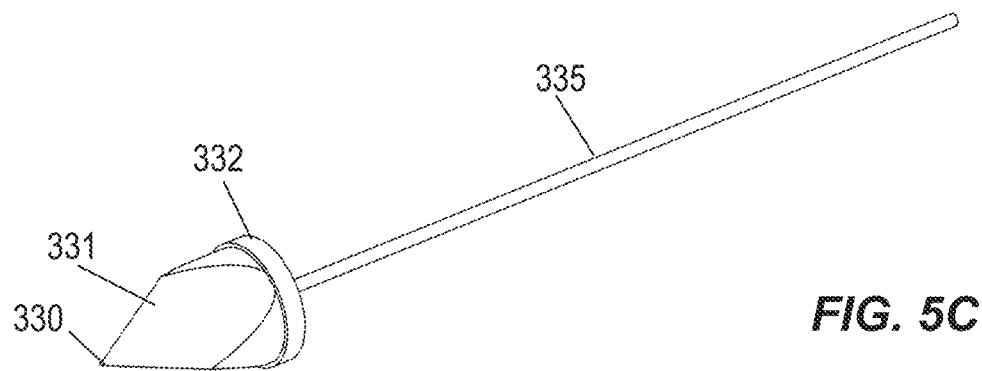
FIG. 5C is a perspective view of the retractable tip member of the steerable surgical device of FIGS. 4A-4B.

FIG. 5C is a perspective view of the retractable tip member 330 of the steerable surgical device 300 of FIGS. 4A-4B. The retractable tip member 330 includes (e.g., three) blade surfaces 331 proximate to an end thereof, terminating at a collar 332 of increased diameter relative to a portion of the tip member 330 that defines the blade surfaces 331, wherein the collar 332 serves as a forward travel stop when the blade surfaces 331 extend through the aperture 346 defined in the moveable tray member 340 of FIG. 5B, and the collar 332 additionally contacts a tissue sample when the retractable tip member 330 is pulled rearward through the longitudinal passage 308 (shown in FIG. 5A). The retractable tip member 330 further includes a guidewire 335 that extends in a longitudinal direction and that may be used to push the retractable tip member 330 forward (e.g., to engage the movable tray member 340 of FIG. 5B, and to push the movable tray member 340 into an extended or deployed state) and to pull the retractable tip member 330 rearward (e.g., to remove the retractable tip member 330 and a corresponding tissue sample through the longitudinal passage 308 shown in FIG. 5A).

Referring back to FIGS. 4A-4B, the steerable surgical device 300 may be used for sequential removal of a plurality of samples (e.g., excisions) from tissue, without requiring complete removal of the steerable surgical device 300 from tissue in which the device is inserted. In certain embodiments, the steerable surgical device 300 may be used for performing a lumpectomy procedure to remove multiple tissue samples from a target area, without undue tissue trauma that would otherwise be inflicted if it were necessary to repeatedly remove and reinsert the entire steerable surgical device in tissue (e.g., of a patient). A method for sequential removal of multiple tissue samples from a target area may include multiple steps. One step includes inserting a portion of the steerable surgical device into the tissue to arrange moveable tray member at a first position in the tissue, wherein such step may include actuation of tendons of the device to change the shape thereof by effectuating pivotal movement between tubular body members separated by a flexible joint. Another step includes extending the retractable tip member to an extended state to position the moveable tray member at a first position in the tissue. Another step includes drawing a first tissue sample through at least one lateral opening into the longitudinal passage of the steerable surgical device, while the moveable tray member is positioned at the first position. A further step includes withdrawing the tip member through the longitudinal passage to extract the first tissue sample from the base end of the steerable surgical device (e.g., through the tubular body members and joint member(s)), while the portion of the steerable surgical device remains in the tissue. Withdrawing of the tip member may include pulling on a guidewire affixed to the tip member. Another step includes returning the tip member through the longitudinal passage (e.g., through the tubular body members and joint member(s)) to contact the moveable tray member proximate to the distal end of the device. Returning of the tip member may include pushing on a guidewire affixed to the tip member. Still another step includes moving the steerable surgical device to a second position in the tissue without completely removing the steerable surgical device from the tissue. Another step includes drawing a second tissue sample through the at least one lateral opening into the longitudinal passage, while the moveable tray member is positioned at the second position. Another step includes withdrawing the tip member through the longitudinal passage (e.g., through the tubular body members and joint member(s)) to extract the second tissue sample from the base end of the steerable surgical device.

Figure 6A:
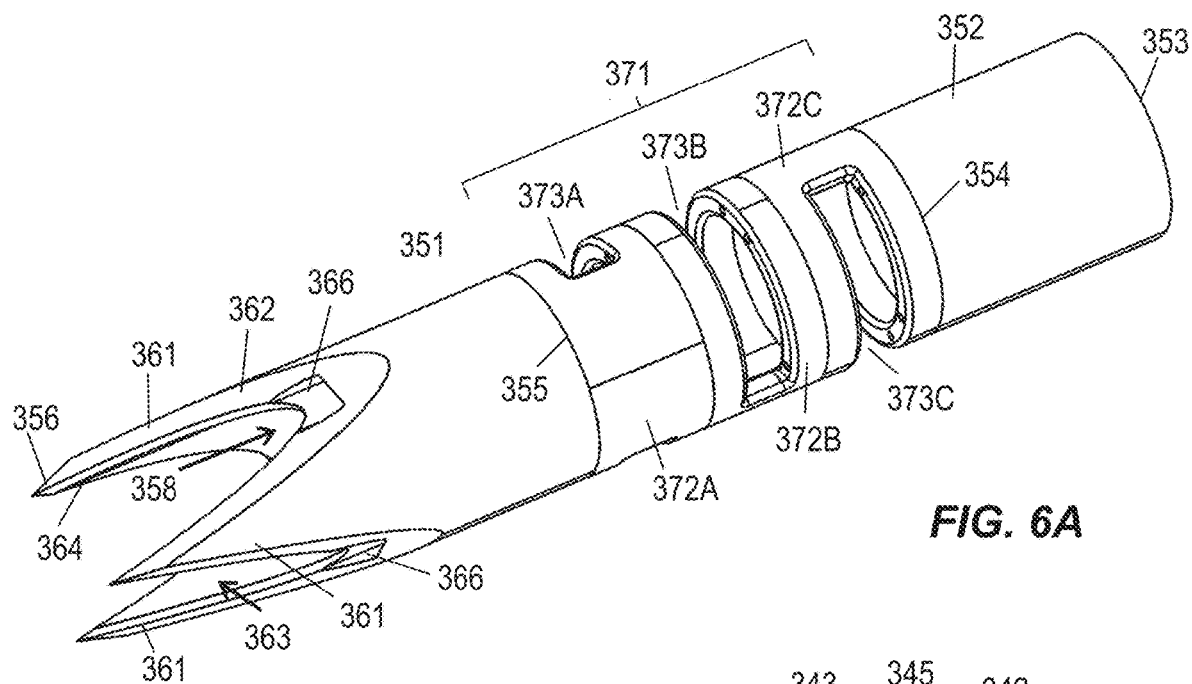
FIG. 6A is a perspective view of a portion of a steerable surgical device according to another embodiment, including a flexible joint that incorporates multiple transverse slits oriented in different directions being disposed between first and second tubular body members, with the first tubular body member comprising three longitudinally projecting portions.

FIG. 6A is a perspective view of a portion of a steerable surgical device according to another embodiment, including a flexible joint 371 that incorporates multiple transverse slits 373A-373C oriented in different directions being disposed between first and second tubular body members 351, 352. As shown, the flexible joint 371 includes first to third joint body segments 372A-372C that define the transverse slits 373A-373C, but in certain embodiments multiple transverse slits may be defined in a single continuous member. The flexible joint 371 is positioned between a proximal end 355 of the first tubular body member 351 and a distal end 354 of the second tubular body member 352. The tubular body members 351, 352 and the joint member 371 in combination form a tubular body structure extending from a proximal end 353 to a distal end 356. The first tubular body member 351 includes first to third longitudinally projecting portions 361 at the distal end 356, with cutting surfaces 362 at surfaces bounding gaps 363 between the longitudinally projecting portions 361. Anchoring points 366 for receiving internal tendons (e.g., SMA actuating tendons, or metal wires to be mechanically tensioned) are additionally provided at portions of the first tubular body structure 351 between the longitudinally projecting portions 361. Longitudinal slots 364 are further defined by the longitudinally projecting portions 361, to receive longitudinal rails 345 of the moveable tray member 340 shown in FIG. 6A. A longitudinal passage 358 extends through the tubular body members 351, 352 and the joint 371.

Figure 6B:
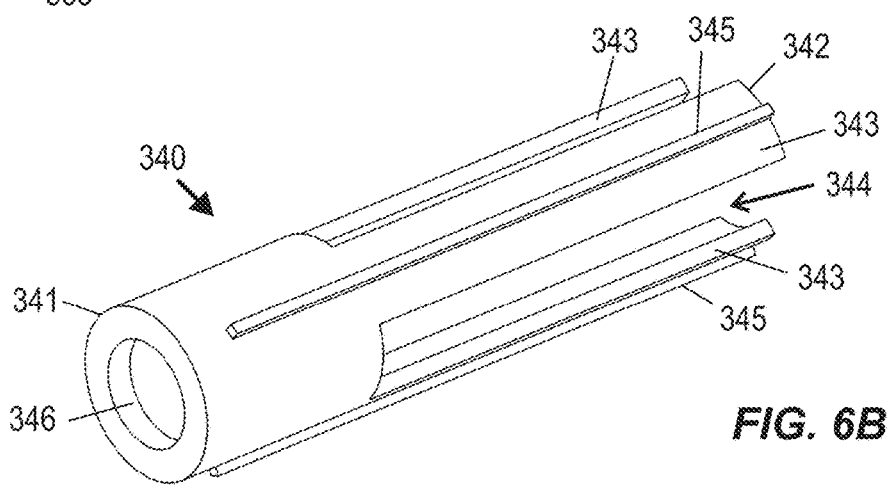
FIG. 6B is a perspective view of a moveable tray member useable with the steerable surgical device portion of FIG. 6A.
Figure 6C:
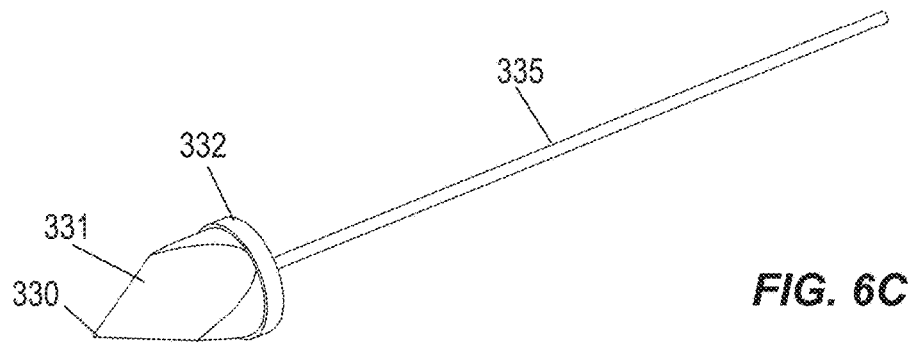
FIG. 6C is a perspective view of a retractable tip member useable with the steerable surgical device portion of FIG. 6A and the movable tray member of FIG. 6B.

FIG. 6B shows a moveable tray member 340 identical to that shown in FIG. 5B, and FIG. 6C shows a retractable tip member 330 identical to that shown in FIG. 5C, wherein the moveable tray member 340 and the retractable tip member 330 are configured to cooperate with the first body member 351 and remaining structures of FIG. 6A in substantially the same manner as described in connection with FIGS. 4A to 5C.

Figure 7:
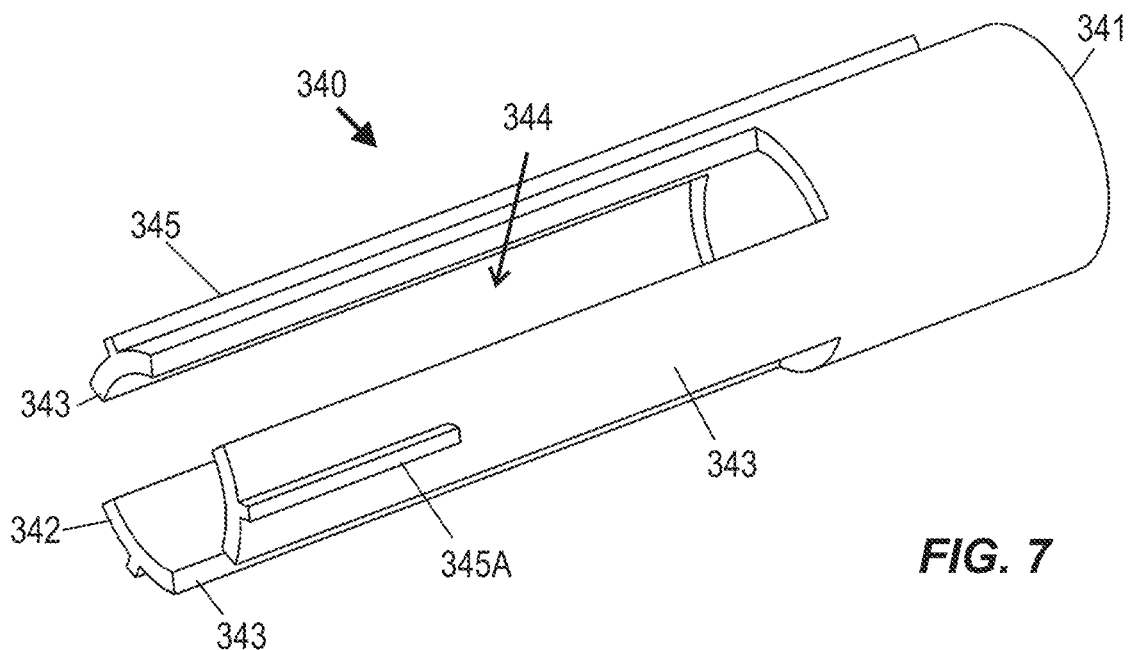
FIG. 7 is reoriented perspective view of the moveable tray member of FIGS. 5B and 6B.

FIG. 7 is reoriented perspective view of the moveable tray member 340 of FIGS. 5B and 6B. As shown, the moveable tray member comprises a distal end 341 and a proximal end 342, with three tray body portions 343 extending to the proximal end and bounding lateral openings 344 arranged between paired tray body portions 343. Each tray body portion 343 defines a longitudinal rail 345, with one such longitudinal rail 345A being of a shorter length than the others to cooperate with a reduced length slot of a corresponding first body member (301 in FIG. 5A or 351 in FIG. 6A) to restrain forward and/or rearward travel of the moveable tray member 340.

Figure 8:
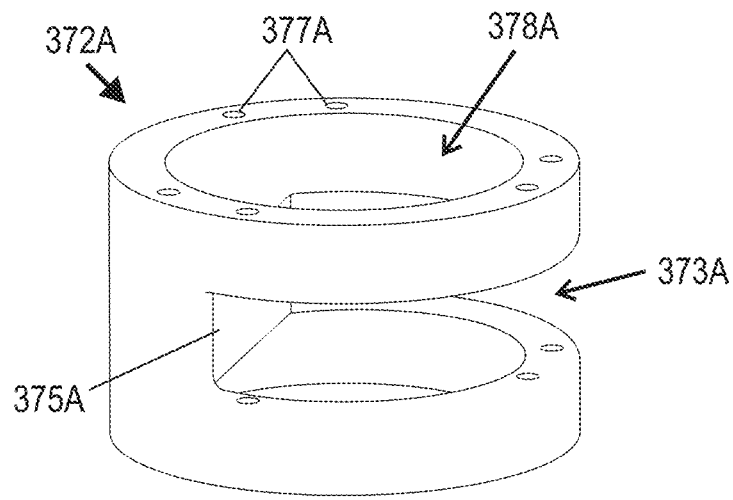
FIG. 8 is a perspective view of a tubular body segment defining a single transverse slit, and useable as part of a joint member shown in FIG. 6A.

FIG. 8 is a perspective view of a tubular body segment 372A defining a single transverse slit 373A (bounded in part by a wall section 375A), and useable as part of the joint member 371 shown in FIG. 6A. A central longitudinal passage 378 is defined through the tubular body segment 372A, while paired through-holes 377A are defined though a wall portion of the tubular body segment 372A to allow passage of tendon members that may be used for actuation of a steerable surgical device incorporating the tubular body segment 372A as part of a joint thereof.

Figure 9:
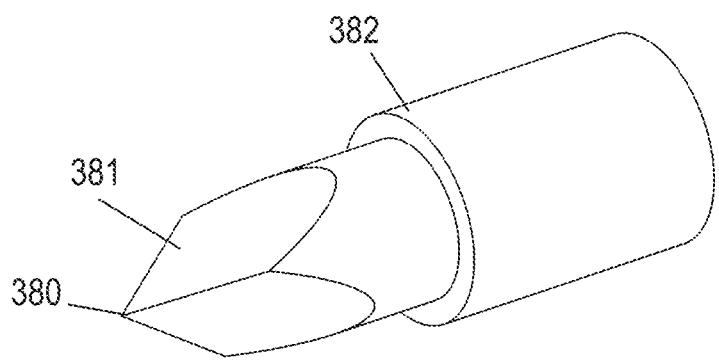
FIG. 9 is a perspective view of an alternative retractable tip member similar to the tip member shown in FIGS. 5C and 6C.

FIG. 9 is a perspective view of an alternative retractable tip member 380 similar to the tip member 330 shown in FIGS. 5C and 6C. The retractable tip member 380 includes (e.g., three) blade surfaces 381 proximate to an end thereof, terminating at a collar 382 of increased diameter relative to a portion of the tip member 380 that defines the blade surfaces 381, wherein the collar 382 serves as a forward travel stop when the blade surfaces 381 extend through the aperture 346 defined in the moveable tray member 340 of FIG. 5B, and the collar 382 additionally contacts a tissue sample when the retractable tip member 380 is pulled rearward through the longitudinal passage 308 (shown in FIG. 5A). The collar 382 of FIG. 9 may include an internal recess (not shown) configured to facilitate engagement with a tissue sample. Although not shown in FIG. 9, it is to be appreciated that the retractable tip member 380 may have associated therewith a guidewire that extends in a longitudinal direction and that may be used to push the retractable tip member 380 forward (e.g., to engage a movable tray member) and to pull the retractable tip member 380 rearward (e.g., to remove a tissue sample through a longitudinal passage of a steerable surgical device).

FIG. 10 is a perspective view of a tubular body 400 into which differently oriented first, second, and third transverse slits 403A-403C are defined to form a flexible joint 404 arranged between body portions 406A-406B extending to ends 401, 402, with the tubular body 400 being useable in a steerable surgical element according to certain embodiments. In certain embodiments, the tubular body 400 may be formed of a metal.

FIG. 11 is a perspective view of a portion of a steerable surgical device 410 including a body structure 415 into which differently oriented groups of first, second, and third transverse slits 413A-413C are defined to form a flexible joint 414. Different numbers of slits are shown for each group of transverse slits 413A (three slits), 413B (two slits), and 413A (one slit). Anchor points 417A, 417B are provided adjacent to or between the groups of transverse slits 413A-413C, for receiving tendon members for deflecting the steerable surgical device 410 at the joint 414 to change the shape thereof. The body structure 415 includes first and second body portions 416A, 416B. A moveable tray member 440 with a fixed tip member 430 are arranged at a distal end 411 of the body structure 415, with the moveable tray member 440 being shown in an extended or deployed state. The moveable tray member 440 includes a tray 441 having a curved profile, with a lateral opening 444 positioned adjacent to the tray 441. The tip member 431 includes blade surfaces 431 that terminal at a tip base 432. In use, the moveable tray member 440 may extended or retracted using a guidewire (not shown) internal to the body structure 415. When the steerable surgical device 410 is inserted to a desired position, the moveable tray member 440 may be deployed, and tissue may be admitted into the lateral opening 414. A distal end 411 of the tubular body 415 may include a cutting surface, such that when the moveable tray member 440 is retracted, a sample of tissue received into the lateral opening 414 into the tray 441 may be cut from the bulk tissue, and received within a longitudinal passage of the steerable surgical device 410. Since the tip member 430 is not retractable separately from the moveable tray member 440, a tissue sample received within the longitudinal passage may only be retrieved by extraction of an entirety of the steerable surgical device 410 from the tissue. In this regard, the steerable surgical device 410 may be suitable for performing biopsy procedures, but may not be as well-suited for sequential removal of multiple tissue samples (e.g., according to a lumpectomy procedure).

Figure 12:
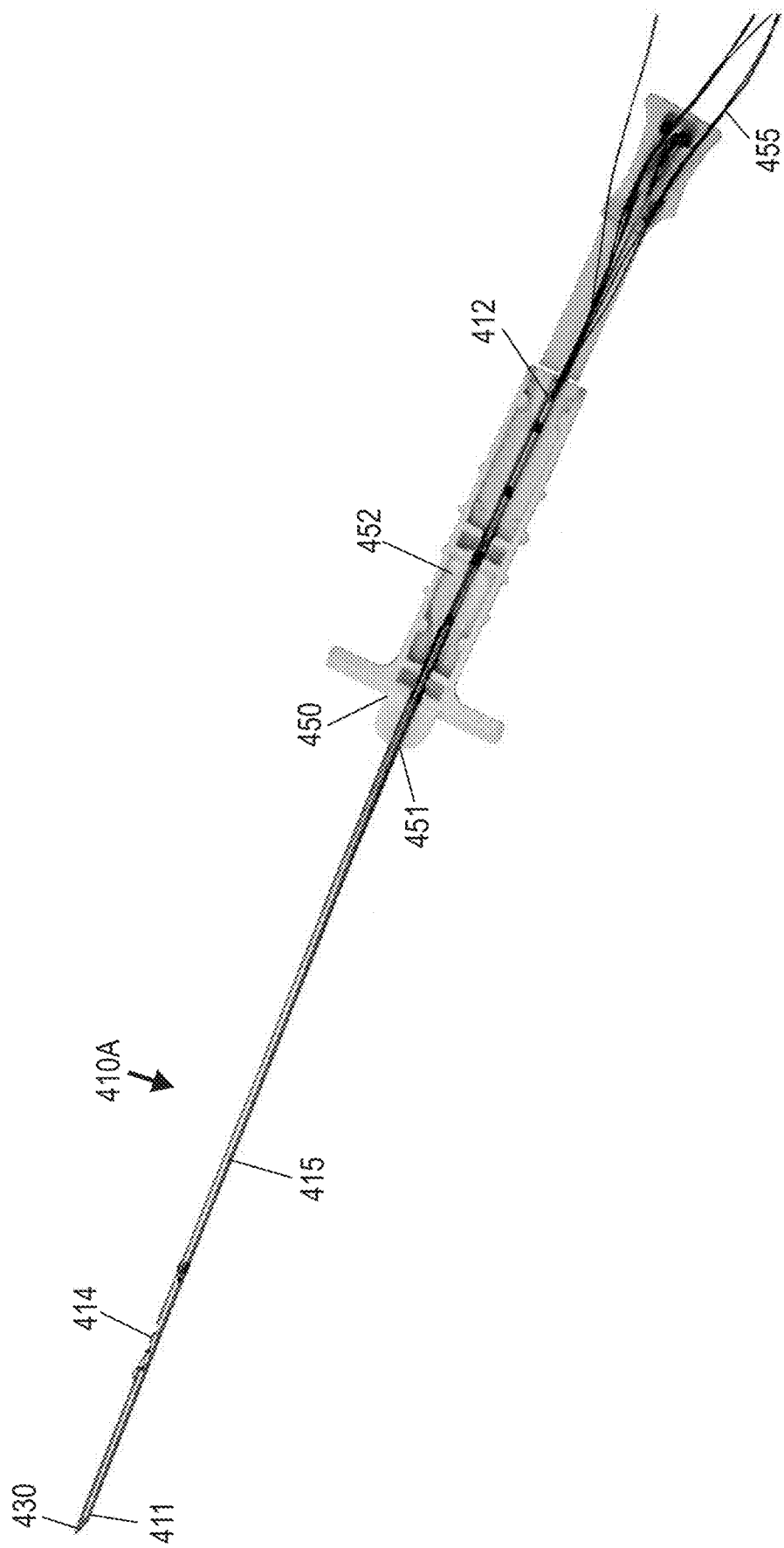
FIG. 12 is a cross-sectional view of a steerable surgical device incorporating the device portion of FIG. 11, further showing a handle supporting the tubular body and showing tendons extending from the handle.

FIG. 12 is a cross-sectional view of a steerable surgical device 410A incorporating the elements of FIG. 11, and further showing a handle 450 supporting the tubular body 415 and showing tendons 455 extending from the handle 450. As shown, the flexible joint 414 is disposed between the handle 450 and a tip 430 arranged at a proximal end 411 of the tubular body 415. A portion of the tubular body 415 is received in an aperture 451 defined by the handle 450, which further includes a cavity 452 therein. A proximal end 412 of the tubular body 415 is arranged within the handle 450, with tendons 455 extending outside the tubular body 415 to enable actuation of the joint 414 (e.g., by applying mechanical tension to the tendons 455, or by applying current to the tendons 455 for heating them if the tendons 455 are SMA actuators).

Figure 13:
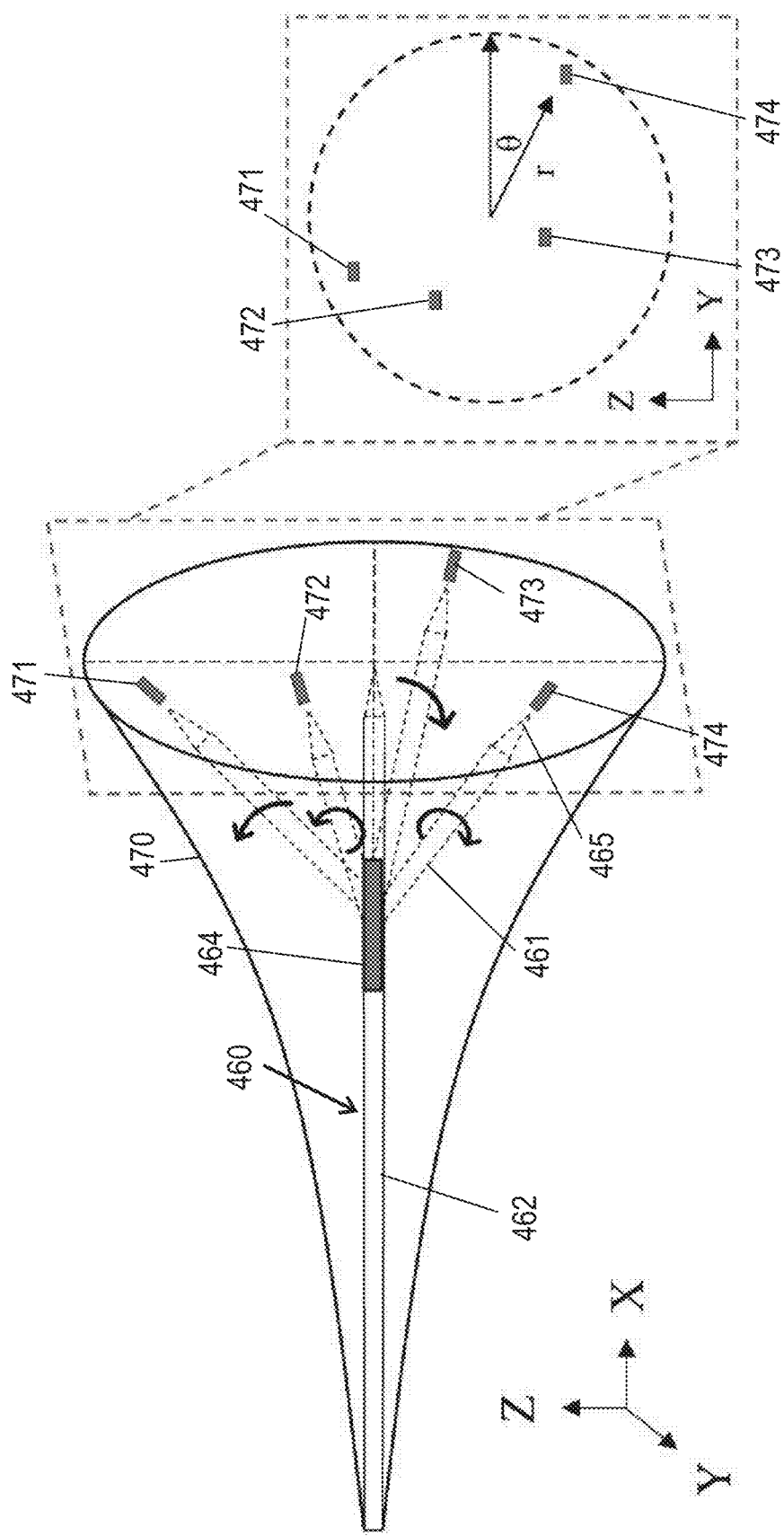
FIG. 13 is a schematic diagram showing deflection of a steerable surgical device into four positions within a generally cone-like boundary volume.

FIG. 13 is a schematic diagram showing deflection of a steerable surgical device 460 (having a flexible joint 464 arranged between first and second tubular body members 461, 462) into four positions within a generally cone-like boundary volume 470. As shown, a tip 465 of the steerable surgical device 460 may be moved to substantially any location within the boundary volume 470 (including the illustrated four exemplary positions 471-474) by causing relative pivotal movement between the tubular body members 461, 462 across the flexible joint 464.

In certain embodiments, ultrasonic imaging may be used in conjunction with active control of a steerable surgical device according to a method for determining position of a tip of the steerable surgical device within tissue, wherein transverse ultrasound probe images and image processing are utilized in combination with saved and predicted tip information to improve identification of a device tip, and compensate for lost positions of the device tip in real time. Such a method may provide improved feedback in robotic-operated or surgeon-operated device insertion procedures. An ultrasound probe is moved concurrently with movement of a steerable surgical device within tissue. Two dimensional transverse ultrasonic images (providing a radial cross section of a tip) are used and processed to estimate tip position. Tip position is important in path planning, steering, and manipulation of an active needle in tissue.

Figure 14:
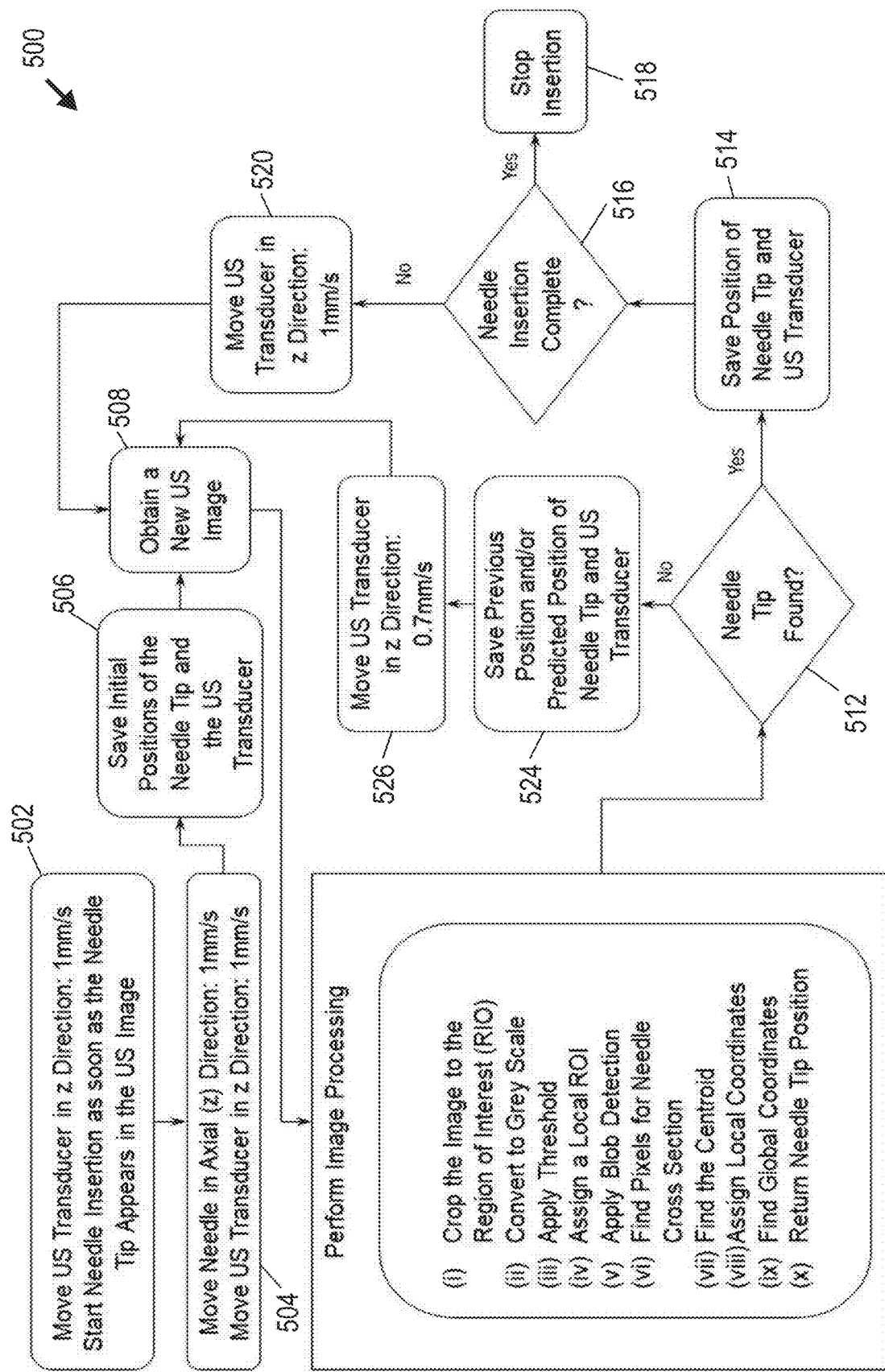
FIG. 14 is a flowchart outlining steps of a method for determining position of a tip of a steerable surgical device within tissue utilizing a robot-assisted ultrasound probe that moves concurrently with motion of the steerable surgical device, and utilizing image processing together with saved and predicted tip position information.

FIG. 14 is a flowchart outlining steps of a method 500 for determining position of a tip of a steerable surgical device (e.g., including or consisting essentially of a steerable needle) within tissue utilizing a robot-assisted ultrasound probe that moves concurrently with motion of the steerable surgical device, and utilizing image processing together with saved and predicted tip position information. The method begins with block 502, in which an ultrasound (US) transducer is moved (e.g., in a z-direction, at 1 mm/s), wherein needle insertion begins as soon as a tip thereof is detected in the ultrasound image. According to block 504, the steerable needle and the US transducer both move in the z-direction (e.g., primary insertion direction perpendicular to a tissue insertion point) at a constant first velocity (e.g., 1 mm/s). In order to estimate the needle tip position, the US image plane must move with the needle tip. Upon curvature of the needle, the US transducer must move (with adjusted (reduced) velocity) along the insertion axis according to the needle tip motion, considering the needle curvature. According to block 506, initial positions of the needle tip and the US transducer are saved. According to block 508, a new US image (e.g., intended to capture the needle tip) is obtained. Multi-step image processing is performed according to block 510. Such image processing steps may include (i) cropping the image to a region of interest (e.g., cropping original 1280×720 images to 715×560 images), (ii) converting the image to grayscale, (iii) applying thresholding to reduce comet tail artefacts (i.e., equally spaced echoes in ultrasonic images that distort a circular shape of a needle image due to reverberation), (iv) assigning a local region of interest, (v) applying blob detection, (vi) identifying pixels in the cross-sectional area of the blob (i.e., needle) within the local region of interest, (vii) finding the centroid of pixels within the cross-sectional area of the blob, (viii) assigning local coordinates to the centroid, (ix) finding global coordinates of the centroid, and (x) returning an identified needle tip position. The method proceeds to decision block 512. If the needle tip is found at decision block 512, then the method proceeds to block 514, at which position information for the needle tip and US transducer are saved, and a check whether needle insertion is complete is performed at block 516. If needle insertion is complete, then insertion is stopped according to block 518; otherwise, the US transducer is moved in the z-direction at the first velocity (e.g., 1 mm/s) according to block 520, and a new US image is obtained according to block 508 and the method returns to block 510 for further image processing. With continued reference to block 512, if the needle tip was not found in a processed image, then the method proceeds to block 524, according to which previously obtained position information and/or predicted position information for the needle tip and US transducer are saved. The method then proceeds to block 526, at which relative speed is adjusted between the US transducer and needle insertion (e.g., by slowing US transducer speed to a second speed, such as 0.7 mm/s), and the method proceeds to block 508 according to which a new US image is obtained.

In view of the content of FIG. 14, in certain embodiments a method for determining position of a tip of a steerable surgical device within tissue may utilize a steerable surgical device comprising an elongated body structure and a tip, and employ multiple steps. One step includes positioning an ultrasound probe to capture images transverse to the elongated body structure. In certain embodiments, such step may include actuation of tendons of the steerable surgical device to change the shape thereof by effectuating pivotal movement between tubular body members separated by a flexible joint. Another step includes moving the ultrasound probe substantially concurrently with movement of the steerable surgical device. In certain embodiments, movement of the ultrasound probe is automated in relation to movement of the steerable surgical device. Another step includes processing images obtained from the ultrasound probe to determine presence and position of the tip in the image. Another step includes adjusting relative speed between ultrasound probe movement and steerable surgical device movement, responsive to a determination from the image processing that the tip is not present in one or more images captured by the ultrasound probe.

Consistent with the foregoing method, in certain embodiments the adjusting of relative speed comprises reducing speed of movement of ultrasound probe and/or increasing speed of movement of the steerable surgical device. In certain embodiments, the method further comprises saving information indicative of tip position responsive to the image processing. In certain embodiments, the saved information indicative of tip position comprises detected tip position if the tip is determined to be present in a processed image. In certain embodiments, the saved information indicative of tip position comprises a previously detected tip position if the tip is not determined to be present in a processed image. In certain embodiments, the saved information indicative of tip position comprises a predicted tip position if the tip is not determined to be present in a processed image. In certain embodiments, the predicted tip position comprises a position determined by extrapolation of multiple prior tip positions.

Figure 15:
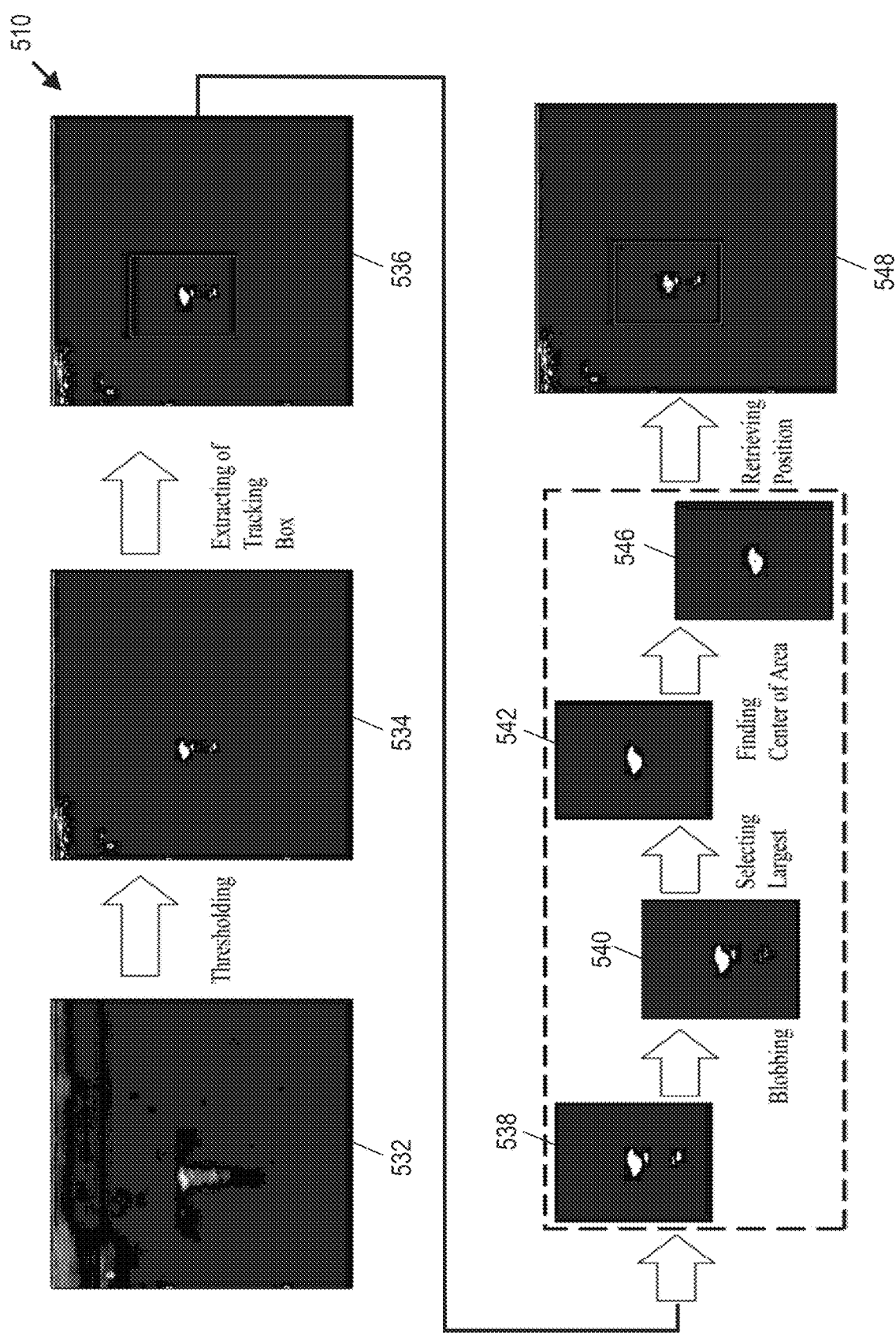
FIG. 15 is a series of frames obtained by processing of transverse ultrasound images according to an experiment utilizing steps outlined in the flowchart of FIG. 14.

FIG. 15 provides a series of frames obtained by processing of transverse ultrasound images according to an experiment utilizing steps outlined in the flowchart of FIG. 14. Needle insertion steps were performed using the device of FIG. 12 inserted into ex vivo beef liver tissue. Different curvatures were realized inside the tissue to a depth of 70 mm, and US images were saved at a sample rate of 15 Hz, resulting in 1051 images. A MATLAP code was developed to fit a second-order polynomial to the lateral and vertical position data, and was used to identify outlier position located in a farther distance compared to the standard deviation of the position data. Upon completion of the needle insertion tasks, the needle was scanned by moving the US transducer from the tissue entry point to the needle tip to find the needle shape. Referring to FIG. 15, a first frame 532 shows an initially cropped US image. A second frame 534 shows the image after grayscale conversion and thresholding. A third frame 536 shows assignment of a local region of interest (rectangular box). A fourth frame 538 is a cropped portion of the third frame 536, confined to the local region of interest. A fifth frame 540 shows the image after blob detection. A sixth frame 542 shows the image after identification of the largest blob and elimination of smaller blobs. A seventh frame 546 corresponds to finding a centroid of the area of the largest blob. An eighth frame 548 corresponds to identification of local and global coordinates of the largest blob (i.e., needle) with superimposition of the local region of interest on the original US image area.

Figure 16:
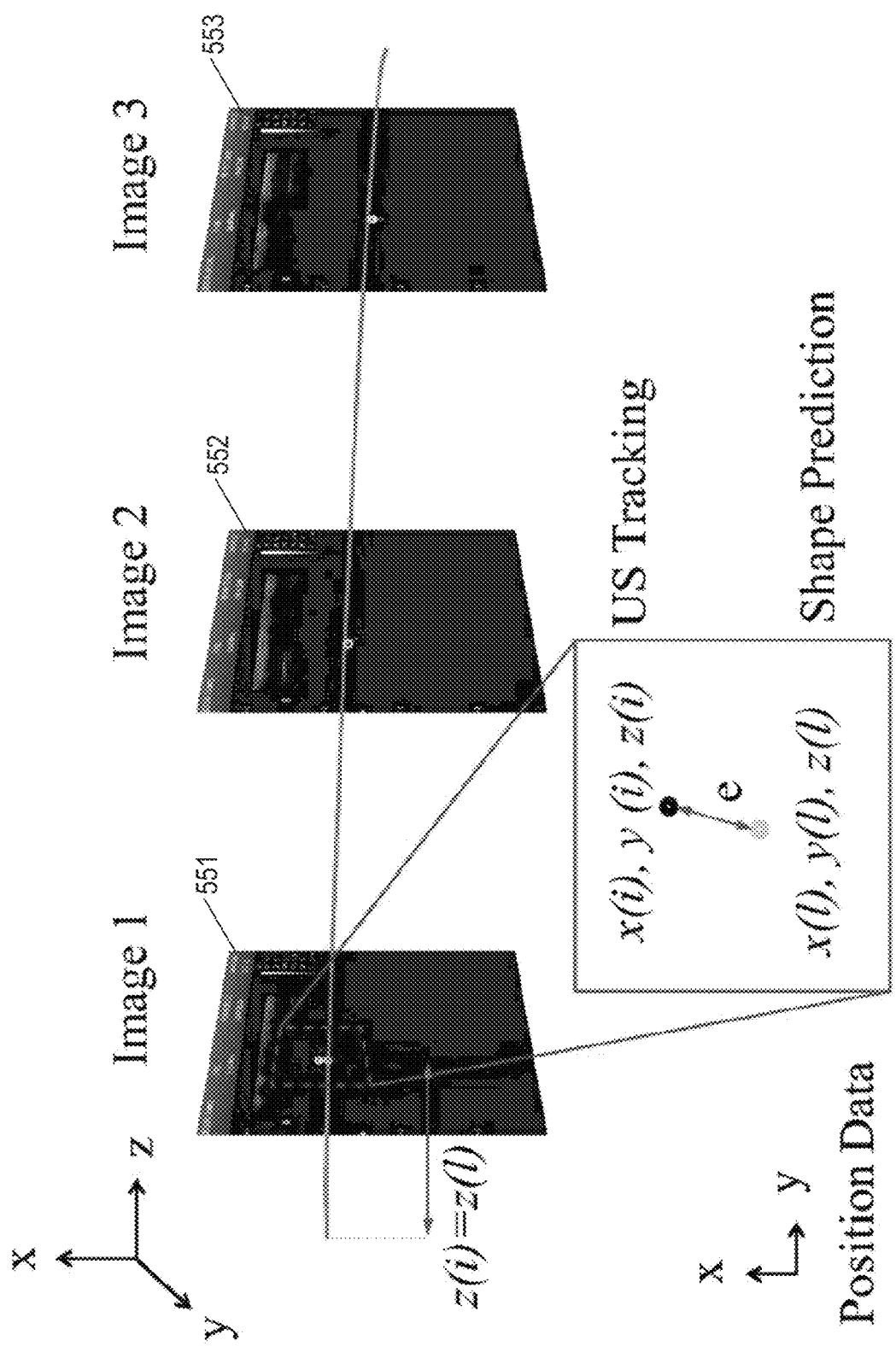
FIG. 16 provides a series of frames corresponding to tip position for a steerable surgical device demonstrating prediction of tip position according to steps outlined in the flowchart of FIG. 14.

FIG. 16 provides a series of frames 551-553 corresponding to tip position for a steerable surgical device demonstrating prediction of tip position according to steps outlined in the flowchart of FIG. 14. A second-order polynomial function was used to model the needle shape, defined by the following equation group:

$$x(I) = a_2 I^2 + a_1 I + a_0$$
$$y(I) = b_2 I^2 + b_1 I + b_0$$
$$z(I) = I \quad \text{(Equations 1)}$$

In the foregoing equation group, I is the needle insertion depth and the values $a_2$, $a_1$, $a_0$ and $b_2$, $b_1$, $b_0$ are the coefficients to be defined. The values x and y represent the spatial position of the needle within the tissue, while z is the depth of the US image. To find the coefficients of this function, position data (spatial coordinates of the needle cross section) from three US images were used for complete parametrization. A MATLAB code was developed to calculate the coefficients of the polynomial function based on three special coordinates along the needle shaft. The polynomial was then used to estimate and plot the 3D shape of the needle after bending inside tissue. The needle was divided into seven segments (each 10 mm long), and the shape of the needle was predicted using second-order polynomials in each segment. The polynomials were defined using (i) unfiltered position data (without removing the outlier positions) and (ii) filtered position data (when the outlier positions were removed). The accuracy of this method to predict the needle shape was estimated by both methods for five needle insertion experiments in the beef liver tissue.

Needle shape was found for seven segments (each 10 mm long) of the needle according to the above-identified experiment. Three transverse US images were chosen in each segment for parametrization of the polynomial functions, and consequently finding the 3D shape of the needle. The insertion depth at which these three US images are obtained is important as different locations of the US images result in different accuracies in shape prediction. A study was performed where US images at various depths were chosen to find polynomial fits. A reasonable agreement between the shape prediction and the needle tip positions was found when the outlier positions are removed (filtered data)

Figure 17A:
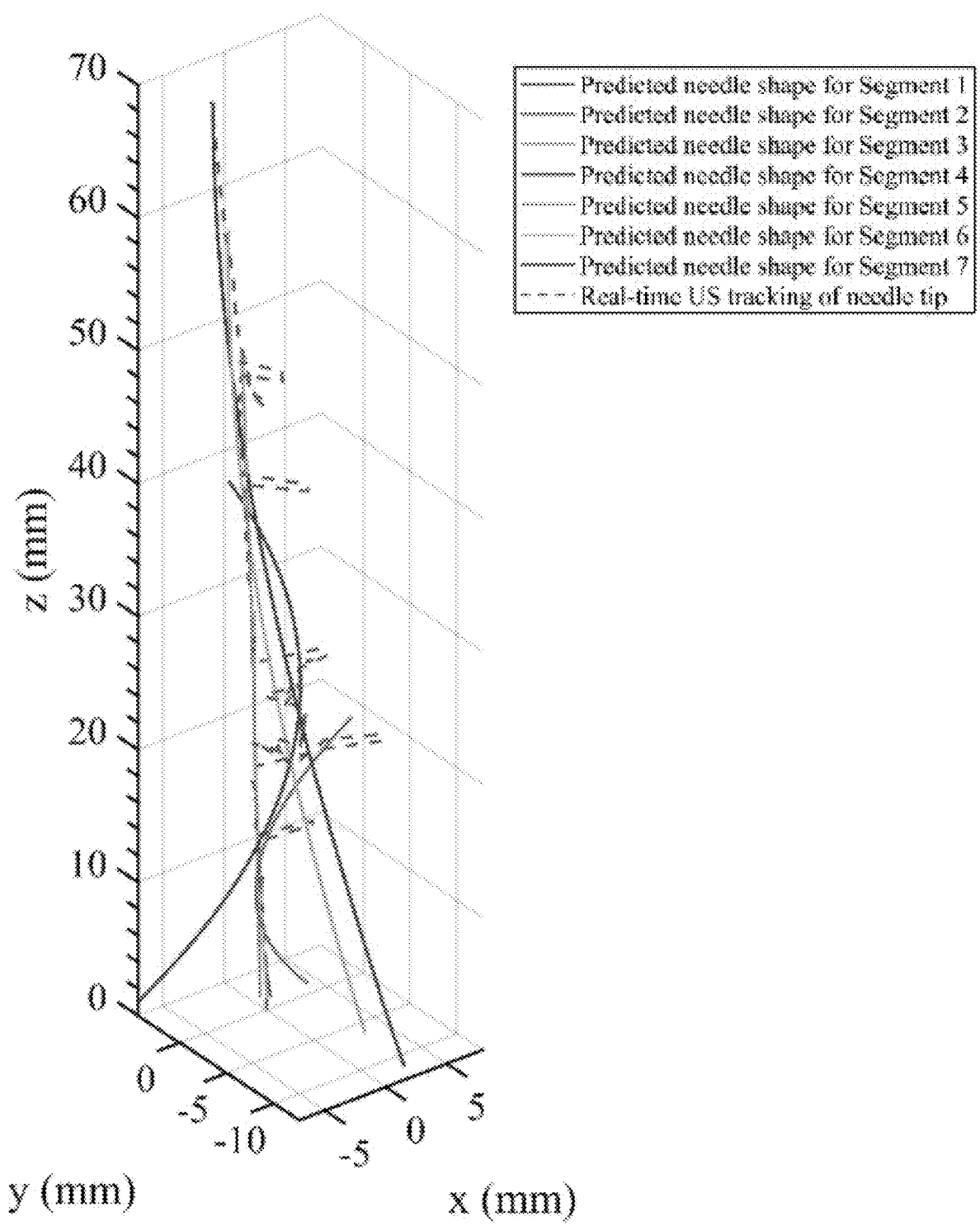
FIG. 17A is a plot of predicted shape generated (according to the steps outlined in FIGS. 15 and 16) from unfiltered data for position of seven (7) 10 mm length segments of a steerable surgical needle in ex vivo beef liver tissue, with a superimposed plot of needle tip position obtained by ultrasound tracking.
Figure 17B:
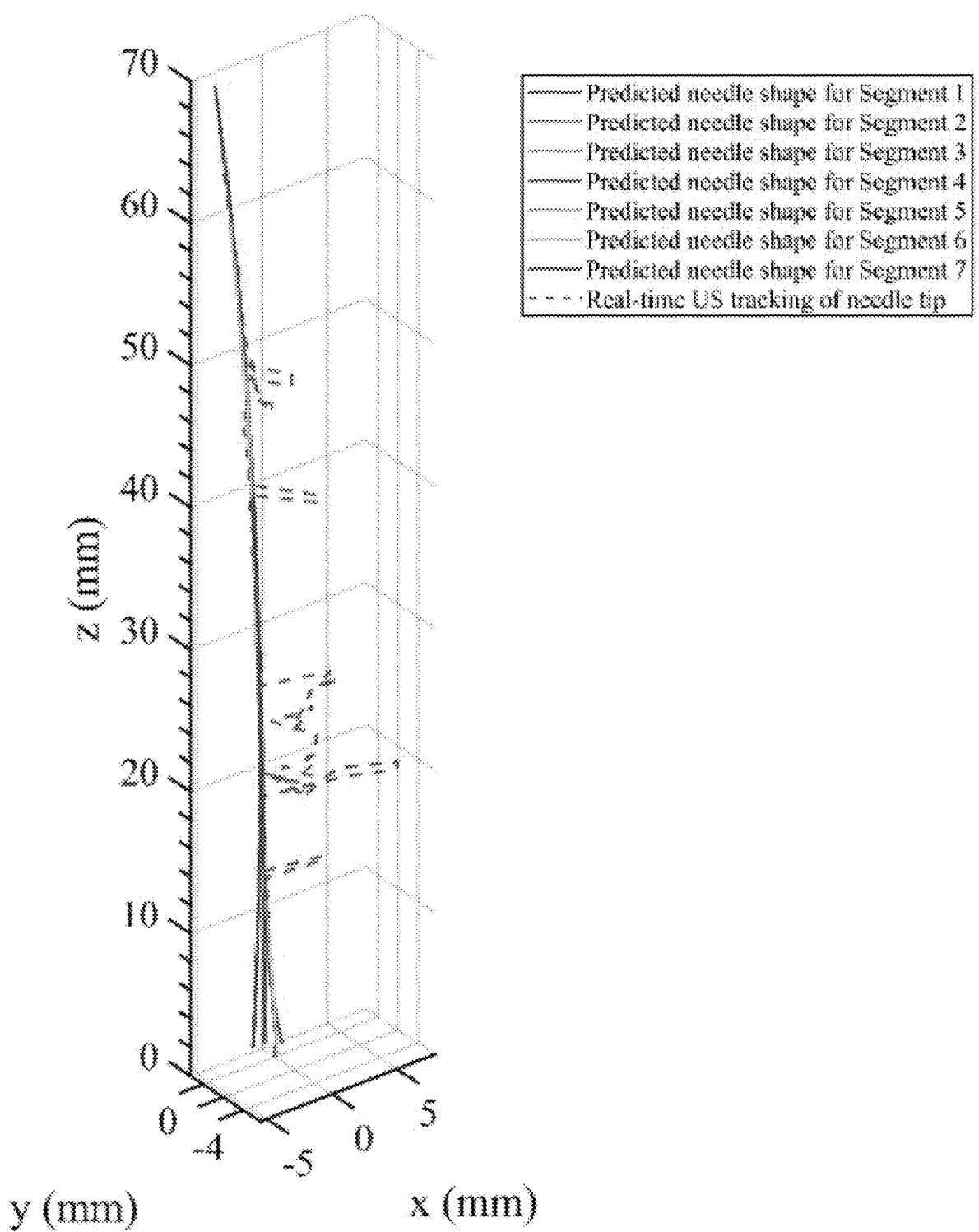
FIG. 17B is a plot of predicted shape generated from filtered data (with outlier positions removed) for position of the seven needle segments in ex vivo beef liver tissue described in FIG. 17, with a superimposed plot of needle tip position obtained by ultrasound tracking.

FIG. 17A is a plot of predicted shape generated (according to the steps outlined in FIGS. 15 and 16) from unfiltered data for position of seven (7) 10 mm length segments of a steerable surgical needle in ex vivo beef liver tissue, with a superimposed plot of needle tip position obtained by ultrasound tracking. The dashed line in FIG. 17A shows presence of outlier data, and the predicted needle shape curves (solid lines) show significant variation for the seven segments. FIG. 17B is a plot of predicted shape generated from filtered data (with outlier positions removed) for position of the seven needle segments in ex vivo beef liver tissue described in FIG. 17, with a superimposed plot of needle tip position obtained by ultrasound tracking. The solid lines in FIG. 17B correspond closely in shape, contrary to the shape variation shown in FIG. 17A, showing the benefit of data filtering. A reasonable agreement between shape prediction and needle tip positions was found for the filtered data.

Figure 17C:
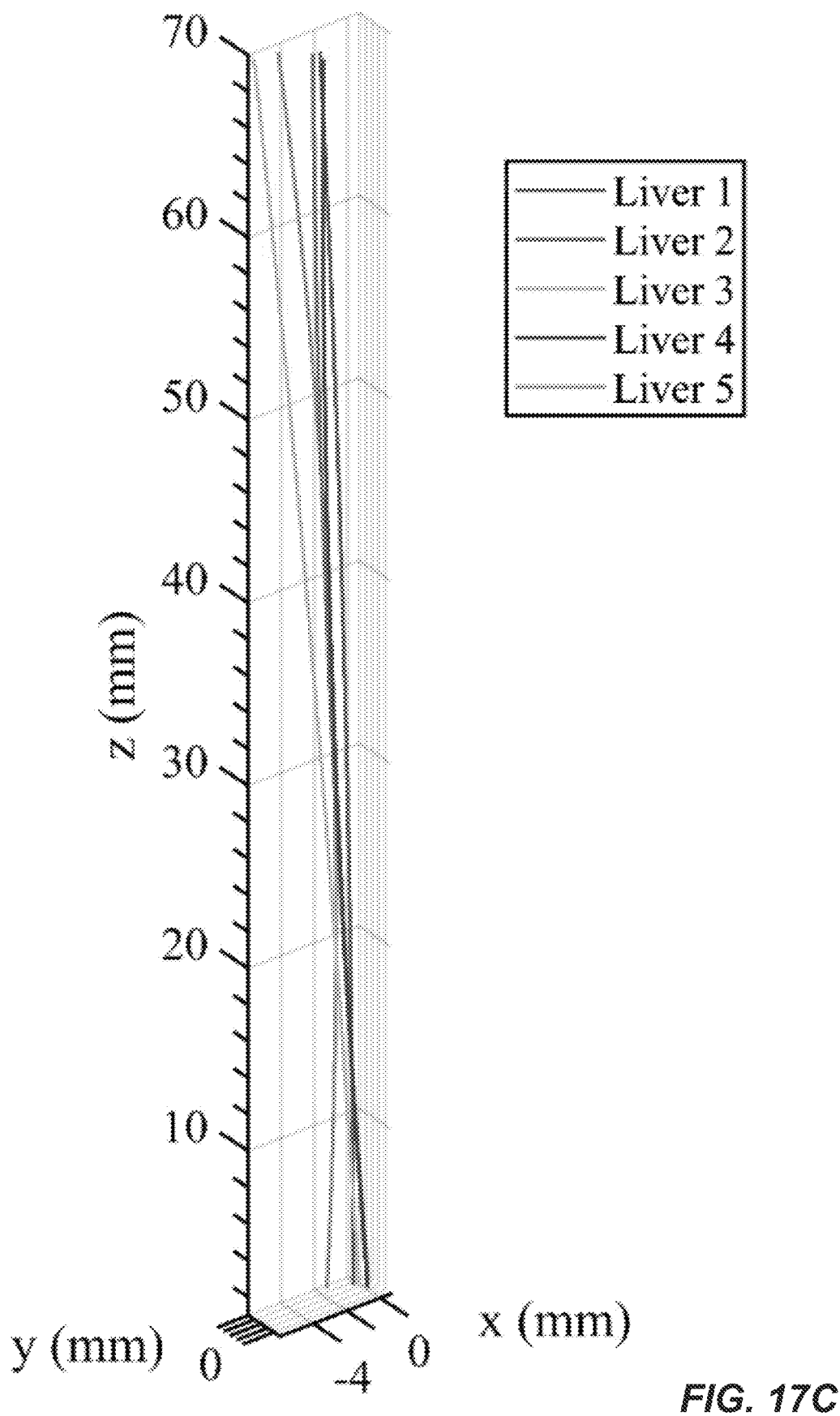
FIG. 17C is a plot of real-time tracking of the tip of a steerable surgical needle obtained by integration of the robot-assisted ultrasound tracking steps and three-dimensional needle shape prediction steps outlined herein, for the five needle insertion tests in ex vivo beef liver tissue.

FIG. 17C is a plot of real-time tracking of the tip of a steerable surgical needle obtained by integration of the robot-assisted ultrasound tracking steps and three-dimensional needle shape prediction steps outlined herein, for the five needle insertion tests in ex vivo beef liver tissue. The distance error between the robot-assisted real-time US tracking and the shape prediction was found using the following Equation 2:

$$e_{z=I} = \sqrt{(x(i)-x(I))^2 + (y(i)-y(I))^2} \quad \text{(Equation 2)}$$

In the foregoing equation, $e_{z=I}$ is the distance error at the depth of/in the needle insertion task, and x(i), y(i), x(I) and y(I) are the lateral and vertical positions of the needle found by US tracking and the lateral and vertical positions of the needle found by shape prediction method, respectively. The area error was first calculated and then divided by the 70 mm of insertion depth to find the average error.

FIG. 17D is a table providing distance error between needle tip positions found by three-dimensional needle shape prediction steps disclosed herein and a robot-assisted ultrasound tracking steps disclosed herein, for manipulation of a steerable surgical needle according to five needle insertion tests in ex vivo beef liver tissue. Average error and maximum error in shape prediction are provided for the whole needle insertion task to the depth of 70 mm. The error was found for unfiltered and filtered position data. It was found that removing outlier positions improves shape prediction (i.e., decreases the average error) by 39% in average. The maximum error was also improved by a great extent (about 86% on average). The large improvement was realized by removing the outlier positions that are extremely far from the median of the position data.

Considering FIGS. 17C-17D, the needle shape prediction on the filtered data was able to match the needle tip position found by the US tracking with an average and maximum error of 0.37 and 0.67 mm, respectively.

During the experiments outlined above, needle tip position was identified about 84% of the time in transverse US images, meaning that needle time position was lost about 16% of the time. To have a reasonable prediction of the lost positions, a filtering method was applied to the position data to remove the outlier positions. Then, 3D needle shape prediction was applied to the data to fill in for the lost positions. Integration of the US tracking, filtering, and 3D needle shape prediction resulted in a reasonable real-time tracking of the needle tip suitable for image guided and closed-loop control of needle insertion procedures.

In certain embodiments, position of a tip within tissue may be determined from sensed SMA properties and sensed compressive force to determine joint deflection of a steerable surgical device, wherein the determined joint deflection is used in conjunction with a joint deflection model to map tip position in tissue without requiring US imaging or other vision-based characterization to be used. To demonstrate feasibility of such a method, kinematic modeling was performed on a multi-link active flexible needle similar to the design of FIGS. 1A-1B. The active needle included three tubular body members, with a base tubular body member being fixed, and with respective body members being separated from one another by two flexible joints. Three NiTi SMA wire actuators (tendons) were integrated into the needle structure to manipulate the needle by effectuating relative pivotal movement of the body members across the joints. The SMA actuators were subject to actuation by resistive or ohmic heating using a triple output programmable DC power supply including sensing of the current and voltage applied to each actuator. A sub-miniature force sensor (Stellar Technology, Inc., Model VLC856-50LB) was affixed to a base of the needle, and coupled to a load cell amplifier (AVIA Semiconductor Co. Ltd, Model HX71) including a programmable gain amplifier (PGA) and a high-precision analog-digital converter (ADC), as well as microcontroller (Arduino UNO Ref. 3). The force sensor was useable to measure vertical (Z-direction) forces acting on the needle during actuation (i.e., needle actuation force). Pre-stress in the form of 40 g mass was applied to each SMA actuator (providing 5.55 MPa prestress per actuator) and each SMA actuator was trained with 80 cycles of heating and cooling.

Figure 18:
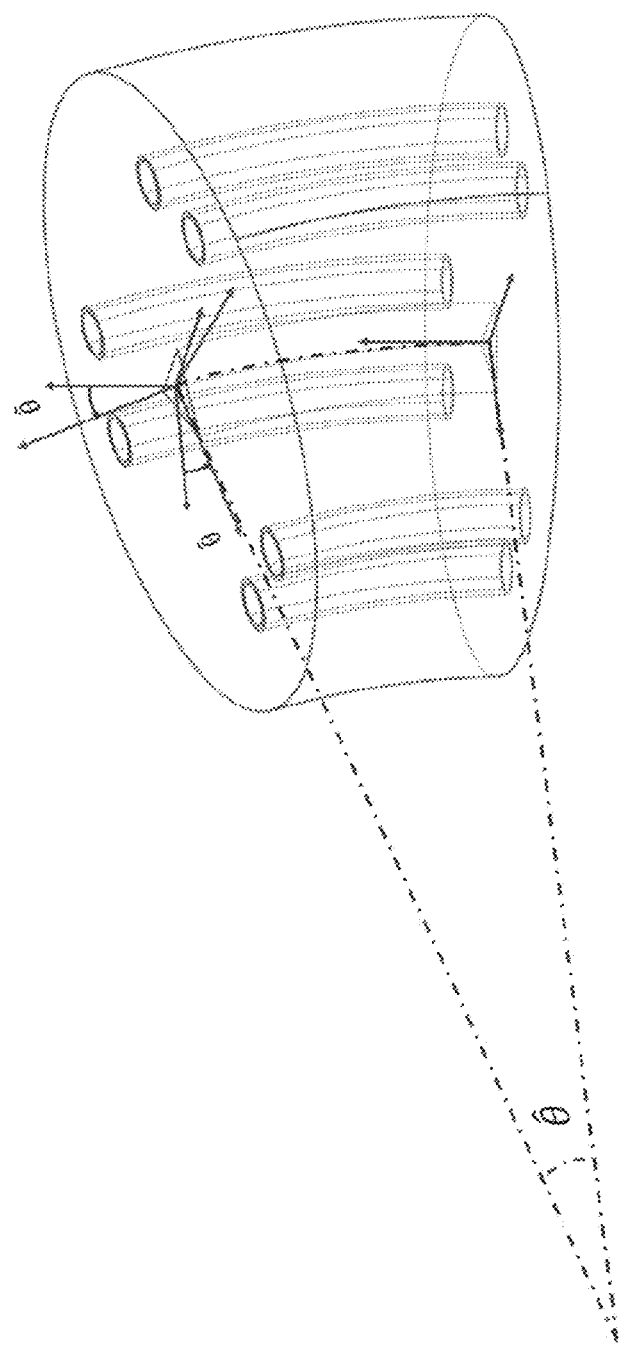
FIG. 18 is a schematic illustration of a deflected flexible joint of a steerable surgical device as disclosed herein.

The stress and strain generated under the actuation of SMA actuators instigates elastic deformation of the flexible joints of a steerable needle. A selected elastomeric material (Digital Photopolymer) exhibits non-linear elastic deformation response characteristics, undergoing large deformation under small loads (and embodying a hyperelastic material). Deformation (i.e., changes in geometric shape) of the flexible joints allows relative pivotal movement between rigid tubular body members of a steerable needle. The deformed shape of the joint is assumed to be an arc of a circle delivering a rotation by the deformation angle $\hat{\theta}$, about the defined actuation axis for the SMA-wire actuator under actuation duties. FIG. 18 shows a schematic illustration of undergone deformation of the flexible joints of the active needle with the deformation angle of the joint introduced as $\hat{\theta}$.

Figure 19:
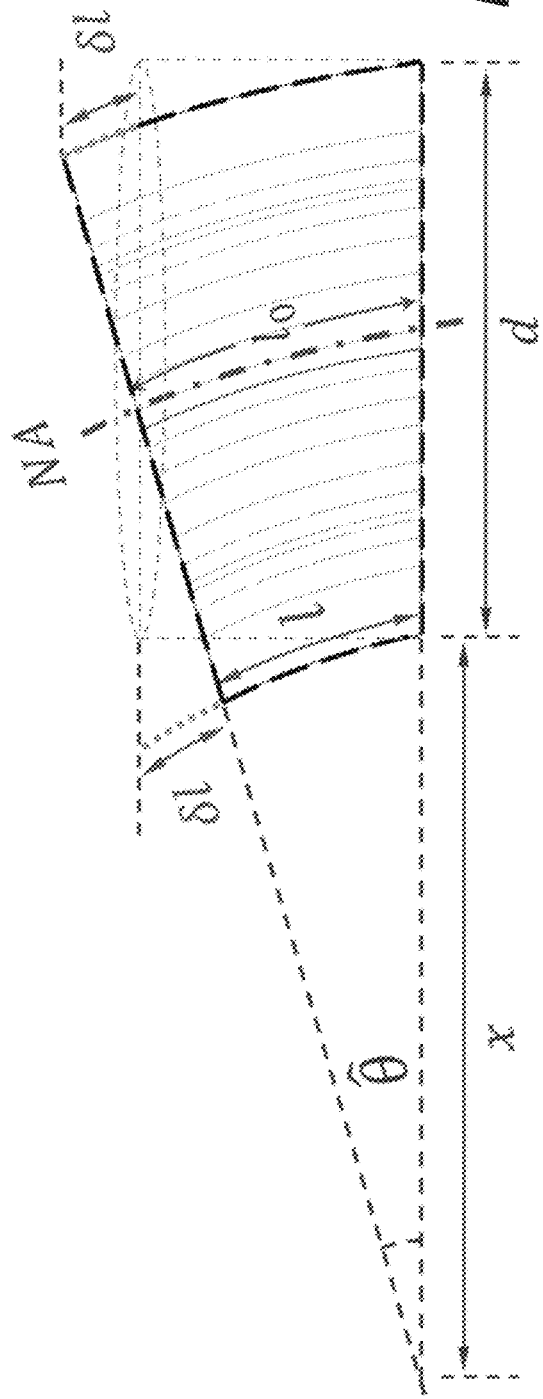
FIG. 19 is a diagram providing kinematics parameters of the deflected flexible joint of FIG. 18.

The deformation angle $\hat{\theta}$ is calculated by the stretch ratio. Due to the symmetry, the neutral axis passes through the centroid of the joint's cross section as shown in FIG. 19. Therefore, the longitudinal strain at the centroid is zero, hence, the length of the centroidal axis is the same as the initial length of the joint, $L_0$. Calculation proceeds as follows:

$$\begin{cases} l_0 - \delta l = x \cdot \hat{\theta} \\ l_0 + \delta l = (x+d) \cdot \hat{\theta} \end{cases} \rightarrow \begin{cases} 2\delta l = d \cdot \hat{\theta} \end{cases}$$

$$\hat{\theta} = 2\frac{\delta l}{d}$$

$$\hat{\theta} = 2\frac{l_0 - l}{d}$$

(Equations 3)

Dividing both sides of the preceding top equation by $I_0$:

$$\frac{\hat{\theta}}{l_0} = 2\frac{\frac{l_0 - l}{l_0}}{d}$$

$$\lambda = \frac{l}{l_0}$$

$$\frac{\hat{\theta}}{l_0} = 2\frac{1-\lambda}{d}$$

$$\hat{\theta} = 2\frac{l_0}{d}(1-\lambda)$$

(Equations 4)

The deformation angles of the flexible joints of the needle determines the deflection of the needle, and the needle tip position during the actuation duties. Specifying the deformation angles of the flexible joints, calculates the position of the tip of the needle as:

$$\Delta\chi i = L_1 \sin\hat{\theta}_1 + L_2 \sin(\hat{\theta}_1 + \hat{\theta}_2) \quad \text{(Equation 5)}$$

$\Delta\chi i$ is the displacement in direction of the actuation axis $\chi i$ for the corresponding SMA-wire actuator, Li is the link length for the i-th link of the needle, and $\theta i$ is the deformation angle of the i-th joint of the needle. FIG. 4 demonstrates the kinematics analysis that leads to derivation of the equation for the needle tip position based on the deformation angles in the flexible joints of the needle under actuation. Assuming equal acting forces on the two flexible joints and equal link lengths simplifies the equation to:

$$\Delta\chi i = L(\sin\theta + \sin 2\theta) \quad \text{(Equation 6)}$$

Figure 20:
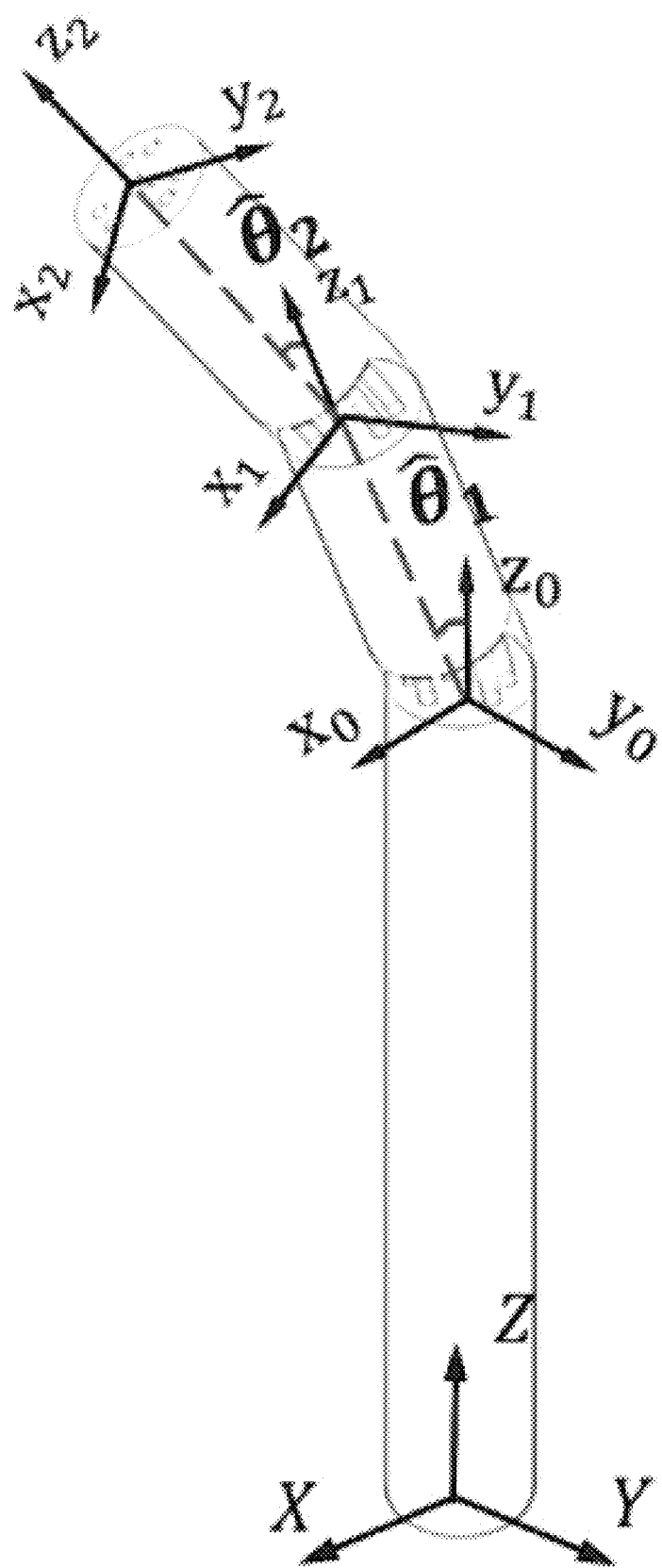
FIG. 20 is a schematic kinematic diagram for a steerable surgical device including three tubular segments with flexible joints arranged between respective pairs of segments.

To design efficient control schemes for active needle steering, kinematics modeling and dynamics analysis of the multi-link flexible needle under the actuation schemes are used. In the kinematics model of the active needle, the flexible joints driven by three SMA-wire actuators were modeled as three nonlinear variable stiffness compression springs[i], delivering a rotation about the actuation axis of the corresponding SMA-wire actuator. The model concept is shown in FIG. 20.

According to certain embodiments, hyperelastic materials may be used as joints in steerable surgical devices. Hyperelastic materials such as elastomers exhibit highly nonlinear elastic response characteristics. Hyperelastic materials undergo large deformations under small, applied loads and retain their initial configuration upon removal of the load. The stress-strain characteristics of hyperelastic materials are quantified through hyperelastic constitutive models constructed by defining the strain energy density of the hyperelastic material as a function of its deformation gradient[ii].

The Ogden model[iii] is a phenomenological hyperelastic model that defines the strain energy density function of a hyperelastic material based on the specific Helmholtz free energy, and is expressed in terms of the principal stretches $\lambda_1$, $\lambda_2$, $\lambda_3$. The strain energy density function (the energy per unit volume stored in the deformed material) for an isotropic hyperelastic material in Ogden model is given by:

$$W(\lambda_1, \lambda_2, \lambda_3) = \sum_{k=1}^{N} \left(\frac{\mu_k}{\alpha_k}(\lambda_1^{\alpha_k} + \lambda_2^{\alpha_k} + \lambda_3^{\alpha_k} - 3)\right) + W_{volume}(J) \quad \text{(Equation 7)}$$

where $\mu_k$, and $a_k$ are material constants, J is the ratio of the deformed and undeformed volumes, and N is the number of terms in the function. The material constants $\mu_k$, and $a_k$ express the shear response of the material. The principal stretches $\lambda_i$ are defined as the ratio of the deformed length $l_i$ to the undeformed length $L_i$, along the principal axes of the Cartesian coordinate system. The stretch ratios in undeformed state are equal to 1.

Under the assumption of incompressibility, the stretch ratios satisfy the incompressibility constraint $\lambda_1\lambda_2\lambda_3=1$. For an incompressible hyperelastic material, J=1, and the volumetric response function $W_{volume}(J)=0$. The principal Cauchy stresses, and the first and second Piola-Kirchhoff stresses for an isotropic hyperelastic material are given by:

$$\sigma_i = \lambda_i \frac{\partial W}{\partial \lambda_i} - p, i \in \{1, 2, 3\} \quad \text{(Equation 8)}$$

$$P_i = \frac{\partial W}{\partial \lambda_i}, S_i = \frac{1}{\lambda_i}\frac{\partial W}{\partial \lambda_i} \quad \text{(Equation 9)}$$

where p, is hydrostatic pressure enforcing the incompressibility constraint, and determined from boundary conditions.

Under uniaxial compression/tension loadings, the principal Cauchy stresses, and corresponding stretch ratios in the Ogden model for an isotropic incompressible hyperelastic material subjected to the uniaxial compressive/tensile stress σ, parallel to a principal axis of the material (here the first principal axis), are given by:

$$\lambda_1 = \lambda, \lambda_2 = \lambda_3 = \lambda^{\frac{-1}{2}}, \text{ and } \lambda = \frac{l_1}{L_1} \quad \text{(Equation 10)}$$

$$\sigma_1 = \lambda_1 \frac{\partial W}{\partial \lambda_1} - p \quad \text{(Equation 11)}$$

$$\sigma_1 = \sum_{k=1}^{N} \frac{\mu_k}{\alpha_k} \lambda_1^{\alpha_k-1} - p \quad \text{(Equation 12)}$$

$$\sigma_2 = \sum_{k=1}^{N} \frac{\mu_k}{\alpha_k} \alpha_k \lambda_2^{\alpha_k-1} - p = 0 \quad \text{(Equation 13)}$$

Note that $\lambda_2 = \lambda_1^{\frac{-1}{2}}$ \quad (Equation 14)

Then p can be determined from the equation σ2=0, as follows:

$$p = \sum_{k=1}^{N} \mu_k \left(\lambda^{\frac{-1}{2}\alpha_k}\right), \lambda = \lambda_1 \quad \text{(Equation 15)}$$

$$\sigma_1 = \sum_{k=1}^{N} \mu_k \left(\lambda^{\alpha_k} - \lambda^{\frac{-1}{2}\alpha_k}\right) \quad \text{(Equation 16)}$$

Separately, self-sensing characteristics and material characteristics may be modeled for SMA-wire actuators.

The electrical resistance of SMA-wire actuator (R=ρL/A), at phase transition in presence of both martensite and austenite phases (ξ: 1→0), can be estimated, and in presence of the individual martensite (ξ=1), or austenite (ξ=0) phases can be modeled, based on the equations of the SMA resistivity model, respectively:

$$R_{SMA} = \xi R_M + (1-\xi)R_A \quad \text{(Equation 17)}$$

$$R_M = R_{0M} + (T-T_{0M})\frac{\partial R_M}{\partial T} + \sigma\frac{\partial R_M}{\partial \sigma} \quad \text{(Equation 18)}$$

$$R_A = R_{0A} + (T-T_{0A})\frac{\partial R_A}{\partial T} + \sigma\frac{\partial \rho_A}{\partial \sigma} \quad \text{(Equation 19)}$$

∂RM/∂T, and ∂ρM/∂σ, in the equations above, are the correlation coefficients of the resistance-temperature and the resistance-stress, respectively, and are determined experimentally[iv].

To find the temperature dependence coefficient of the resistance of the SMA-wire actuator in martensite phase (∂RM/∂T), a constant electric current input is applied to the SMA wire actuator under constant stress level for a period of time to achieve a steady state condition (energy equilibrium) at a temperature above the ambient temperature (T∞), and below the austenite start temperature (As). The steady state temperature and the steady state resistance of the SMA-wire actuator is measured to calculate the martensite resistance-temperature correlation coefficient (∂RM/∂T) of the SMA-wire actuator.

To obtain the stress dependence coefficient of the resistance of the SMA-wire actuator in martensite phase (∂RM/∂σ), the electrical resistance of the SMA-wire actuator under different stress levels is measured by applying a low constant electric current input while different levels of stress are applied to SMA wire via the attached weights.

To obtain the two linear stress- and temperature-dependence coefficients of the electrical resistance of the SMA-wire actuator in presence of individual austenite phase, the electrical resistance and the temperature of the SMA-wire actuator while undergoing a complete phase transformation via joule heating actuation of the SMA wire under different applied stress levels may be measured by applying multiple constant levels of electric current inputs.

The material properties and nonlinear deformation characteristics of the flexible joints (Digital Photopolymer) were characterized by mechanical testing of the flexible joint's material in a physical compression test. The applied uniaxial compression loads were measured using the force sensor, and vision-based measurement method was used to measure the deformation lengths of the test specimen under the applied loads. The values of the material constants used in the Ogden model, i.e., ak, and μk, were estimated by least squares fitting of the Ogden model (of order 3, i.e., N=3) for isotropic incompressible hyperelastic materials, to experimental data. The least squares method objective is to minimize sum of the squared error, i.e., the difference between the stress values of the measurement and the model equation. Parameterizing the Ogden model parameters via data fitting translates to a nonlinear optimization problem, which demands an iterative numerical solution. This was performed in COMSOL Multiphysics® 5.5 using the optimization module.

Figure 21:
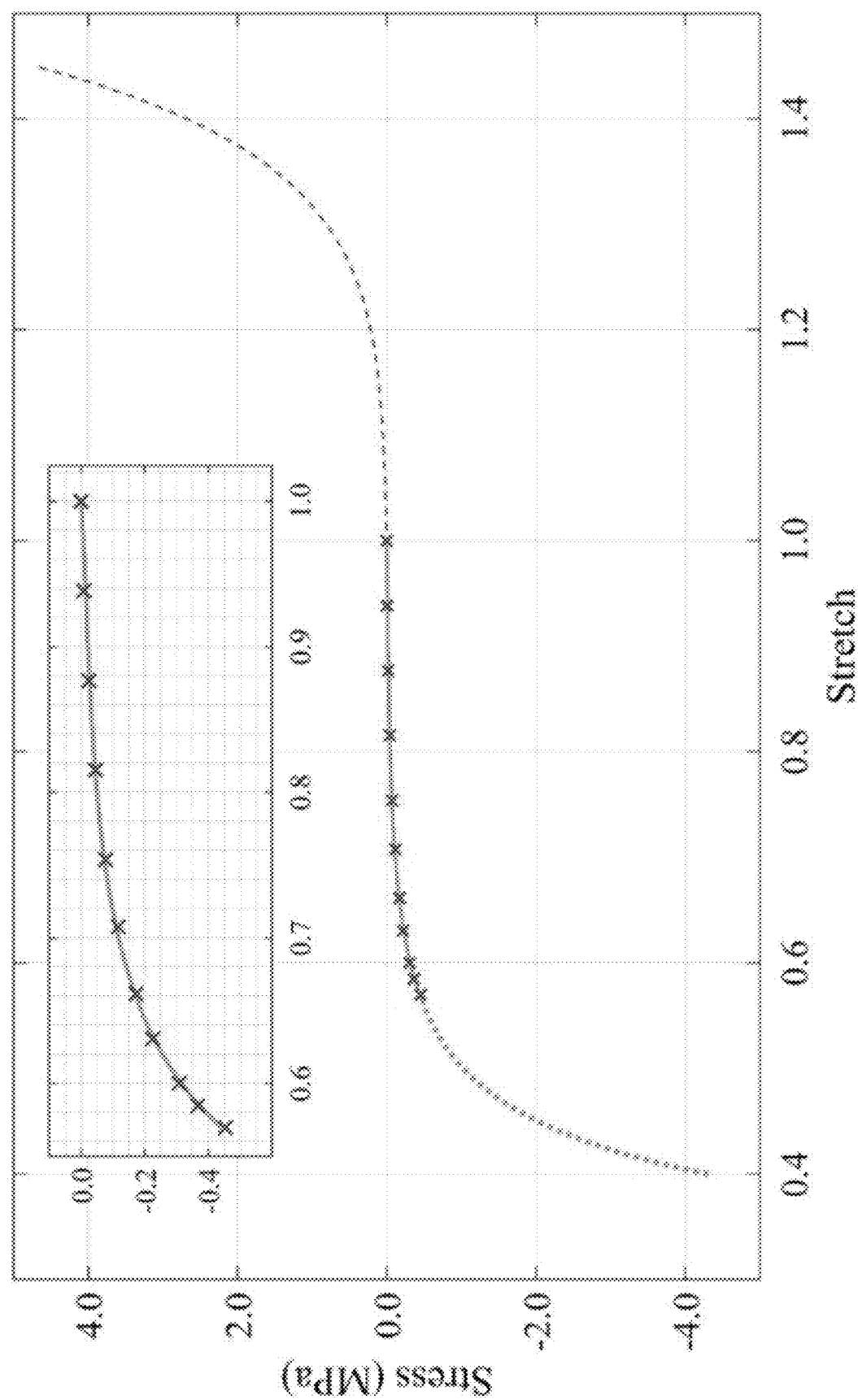
FIG. 21 is a plot of stress versus stretch for a flexible joint based on the Ogden hyperelastic material model, showing non-linear stretch-stress response.

The characteristic stress-stretch response of the flexible joint (Digital Photopolymer) based on the Ogden hyperelastic material model (N=3) with the derived parameter values for $\alpha_i$, and $\mu_i$ is illustrated in FIG. 21.

Figure 22:
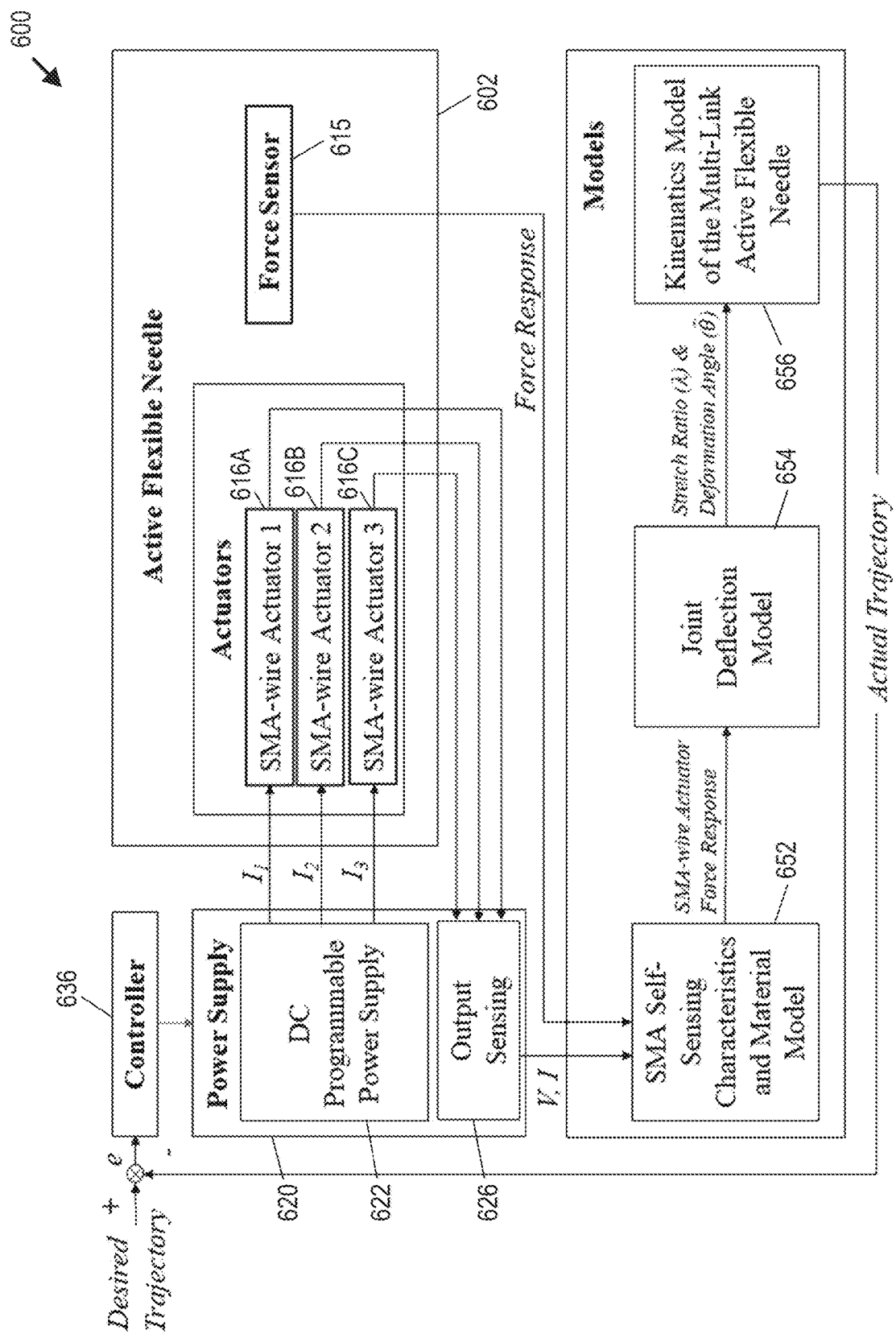
FIG. 22 is a schematic diagram showing use of SMA actuators for actuation and output sensing for joints of a steerable surgical device, and utilization of SMA actuator signals and a sensed compressive force in conjunction with a joint deflection model to determine deflection of at least one joint, followed by utilization of the determined deflection to map position of the tip of the steerable surgical device.

FIG. 22 is a schematic diagram for a control system 600 showing use of SMA actuators 616 for actuation and output sensing for joints of a steerable surgical device (e.g., an active flexible needle) 602, and utilization of SMA actuator signals and compressive force signals obtained from a force sensor 615 (i.e., a sensor arranged to sense compressive force at a base of the steerable surgical device 602) in conjunction with a joint deflection model 654 to determine deflection of at least one joint of the surgical device 602, followed by utilization of the determined deflection to map position of the tip of the steerable surgical device 602. A controller 636 is configured to receive a desired trajectory signal and communicate with a power supply apparatus 620 having a DC programmable power supply module 622 and an output sensing module 626 both coupled to multiple SMA-wire actuators 616A-616C of the steerable surgical device 602. In certain embodiments, the controller 636 may comprise a proportional-integral-derivative (PID) controller configured to control the power supply module 622 to provide appropriate current inputs ($I_1$, $I_2$, and $I_3$) to the SMA-wire actuators 616A-616C based on an error between the desired and the actual trajectories of these actuators 616A-616C. The actual trajectory may be estimated using feedback signals received from the SMA-wire actuators 616A-616C, using position sensing characteristics of the SMA-wire actuators 616A-616C signals received from the force sensor 615. The control scheme presented in FIG. 22 relies on feedback received from the SMA-wire actuators 616A-616C and the force sensor 615 without necessitating a position sensor or vision-based tracking system. Estimating the position of a tip of the steerable surgical device 602 based on the feedback may utilize multiple models, namely, (i) a SMA self-sensing characteristics and material model 652, (ii) joint deflection model 654 for the flexible joints, and (iii) a kinematics model 656 of the steerable surgical device, respectively. The SMA-wire actuators 616A-616C may be used simultaneously as actuators as well as sensors of the system 600.

The SMA self-sensing characteristics and material model 652 estimates the engineering stress provided by each SMA-wire actuator 616A-616C based on voltage and current feedback received from the output sensing module 626 of the power supply 620 and based on signals received from the force sensor 615. The engineering stress (i.e., SMA actuator force response) obtained from the SMA self-sensing characteristics and material model 652 is then used by the joint deflection model 654 for the flexible joints of the steerable surgical device 602 to estimate the stretch ratio (λ) and consequently the deformation angle (θ) for the joints. Ultimately, the kinematics model 656 of the steerable surgical device (e.g., multi-link active flexible needle) is used to estimate the tip position (or actual trajectory) based on the stretch ratio and deformation angle of the flexible joints. Thereafter, the estimated actual trajectory and the desired trajectory may then be compared (i.e., using the controller 636) to estimate the error of the needle tip path tracking and close the control loop. The foregoing steps may be performed in real-time, concurrently with insertion and advancement of the steerable surgical device 602 in tissue, to eliminate the necessity for ultrasonic detection or other (e.g., vision-based) needle detection system. In certain embodiments, the models 652, 654, 656 may operate on the controller 636, or may reside on one or more other controllers or computing devices (not shown) in communication with the illustrated controller 636.

The system 600 illustrated in FIG. 22 is suitable for use in performing a method for tracking position of a tip of a steerable surgical device as disclosed herein, using sensor signals obtained from SMA actuators and a force sensor, and utilizing models (e.g., a joint deflection model and a kinematic model) to determine tip position without requiring the use of ultrasonic imaging or other vision-based imaging. Such a method may include multiple steps. A preliminary step may include positioning steerable surgical device in tissue, the steerable surgical device including at least one tubular joint member (e.g., a joint comprising hyperelastic material, or comprising multiple different oriented transverse slits) arranged between corresponding ones of a plurality of tubular body members, and multiple longitudinally oriented SMA elements arranged in or on the elongated body structure. In certain embodiments, the SMA elements may embody SMA wire actuators (which may also be referred to as SMA actuator tendons). Insertion of a steerable surgical device in tissue may include actuation of tendons (e.g., SMA tendons) of the device to change the shape thereof by effectuating pivotal movement between tubular body members separated by a flexible joint. A further step includes sensing electrical properties of the multiple longitudinally oriented SMA elements, and sensing compressive force at a base end of the steerable surgical device (e.g., using a force sensor). An additional step includes utilizing (i) the sensed electrical properties and (ii) the sensed compressive force to identify force response of the shape memory alloy elements. Another step includes utilizing the identified force response of the shape memory alloy elements, and utilizing a predetermined joint deflection model of the tubular joint member, to determine deflection of the at least one tubular joint member. Another step includes utilizing the determined deflection of the at least one tubular joint member to map position of the tip of the surgical steerable instrument within the tissue.

In certain embodiments, the foregoing method may be supplemented by further sensing at least one of (a) rotation of the steerable surgical device and (b) insertion length of the steerable surgical device to produce sensed information, and further utilizing the sensed information in the mapping of position of the tip of the surgical steerable instrument within the tissue. Although the preceding discussion referred to the use of SMA actuator tendons, in certain embodiments mechanical tendons may be used as actuators, and longitudinal SMA elements may be used solely as sensors.

Figure 23A:
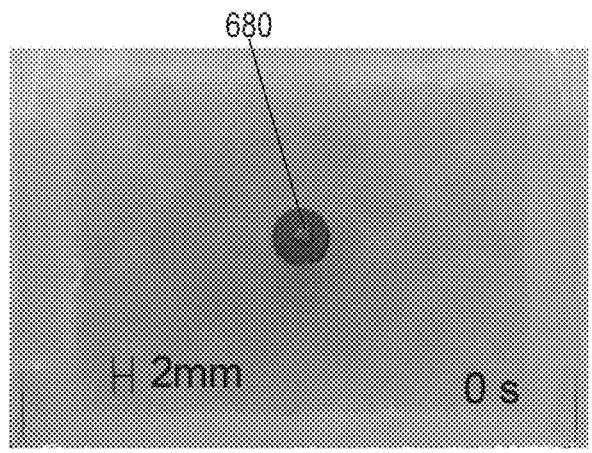
FIGS. 23A-23F are six photographic frames showing position of a needle tip at different times during manipulation of a steerable surgical device in a phantom tissue, with a superimposed triangle tracing a pre-planned needle path.
Figure 23B:
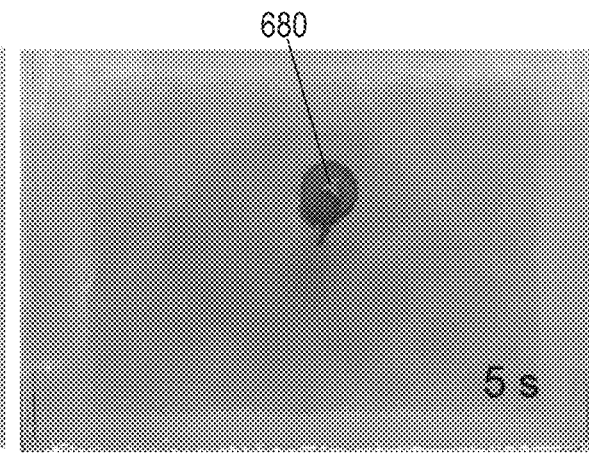
Figure 23C:
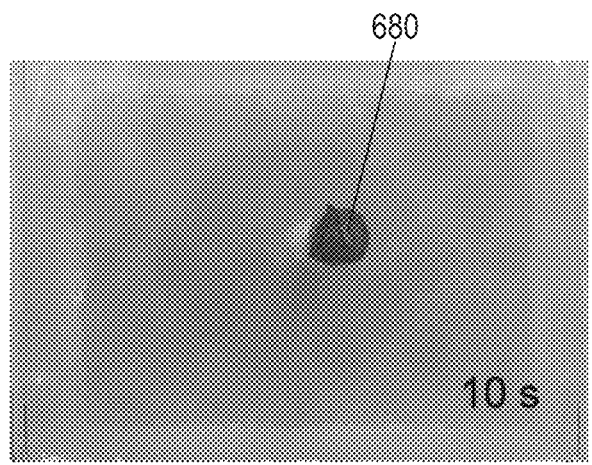
Figure 23D:
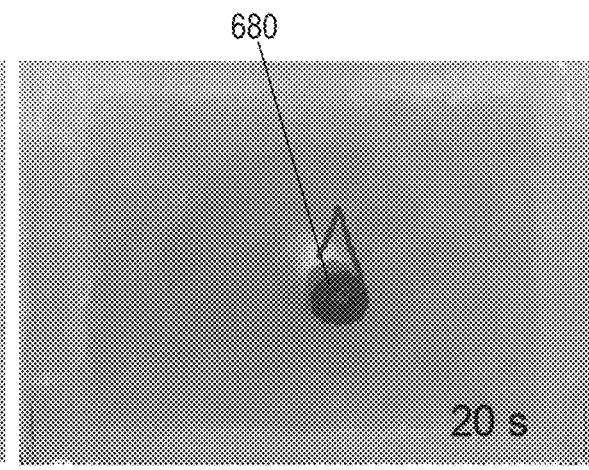
Figure 23E:
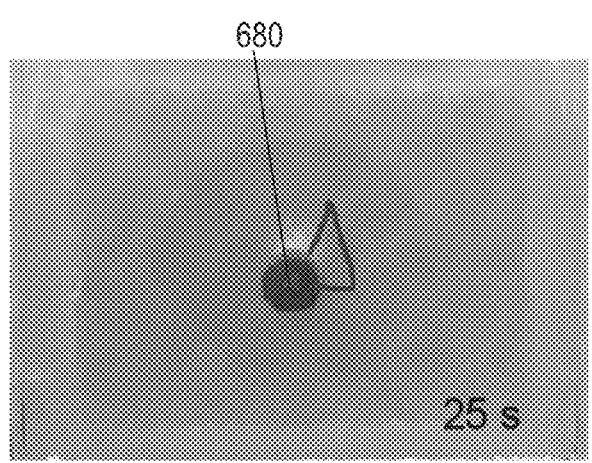
Figure 23F:
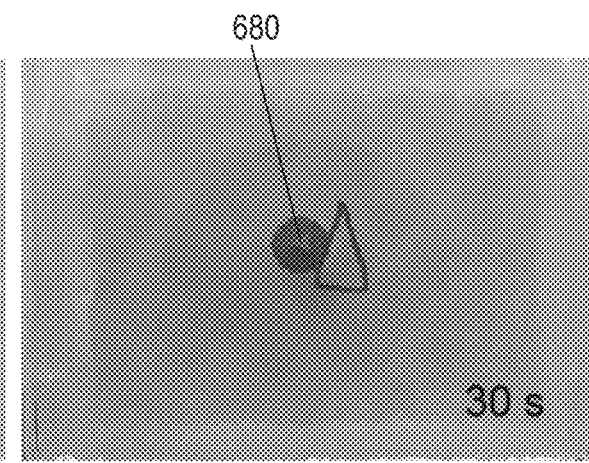

To test the capability of a control program to manipulate the needle tip inside a phantom tissue, a camera was placed on top of the needle while tracing a pre-planned triangular path. A position tracking code was used to capture the tip movement. FIGS. 23A-23F show six frames of movement of a needle tip 680 during operation (i.e., at times of 0 seconds, 5 seconds, 10 seconds, 20 seconds, 25 seconds, and 30 seconds, respectively). A superimposed triangle, or at least portions thereof, is visible in FIGS. 23B-23F, to represent a pre-planned needle path. In FIGS. 23B and 23C, the needle tip 680 is positioned proximate to an upper vertex of a triangle portion. In FIG. 23D, the needle tip 680 is positioned proximate to a lower right vertex of a triangle portion, while in FIG. 23E, the needle tip 680 is positioned proximate to lower left vertex of a triangle In FIG. 23F, the needle tip 680 is shown slightly outside (to the left) of a triangle. It was shown that the active flexible needle is able to track this path with reasonable accuracy without a need for an external position sensor, and by only relying on the sensing capabilities of the SMA-wire actuators.

Those skilled in the art will recognize improvements and modifications to the preferred embodiments of the present disclosure. All such improvements and modifications are considered within the scope of the concepts disclosed herein and the claims that follow.

[i] S. Karimi and B. Konh, "Dynamic characteristics analyses and FEM modeling of flexible joints of an SMA-activated flexible multi-joint needle," in *Design of Medical Devices Conference*, 2020, pp. 1-3.

[ii] M. Shahzad, A. Kamran, M. Z. Siddiqui, and M. Farhan, "Mechanical characterization and FE modelling of a hyperelastic material," *Mater. Res.*, vol. 18, no. 5, pp. 918-924, 2015, doi: 10.1590/1516-1439.320414.

[iii] R. W. Ogden, "Large deformation isotropic elasticity—on the correlation of theory and experiment for incompressible rubberlike solids," Proc. R. Soc. London. A. Math. Phys. Sci., vol. 326, no. 1567, pp. 565-584, 1972, doi: 10.1098/rspa.1972.0026.

[iv] H. Song, E. Kubica, and R. Gorbet, "Resistance Modelling of Sma Wire Actuators," *Aerospace*, 2011.

What is claimed is:

1. A steerable surgical device comprising:
   a tubular body comprising: a central longitudinal axis extending in a longitudinal direction, a base end, a distal end opposing the base end, a plurality of tubular body members including first and second tubular body members arranged between the base end and the distal end, a first tubular joint member arranged between the first tubular body member and the second tubular body member, and a longitudinal passage extending through at least the plurality of tubular body members and the first tubular joint member;
   a plurality of tendon members extending from at least the first tubular body member through the first tubular joint member to the second tubular body member, wherein each tendon member of the plurality of tendon members is independently actuatable to effectuate pivotal movement between the first tubular body member and the second tubular body member; and
   a moveable tray member arranged at the distal end, the moveable tray member comprising at least one lateral opening and being configured to translate in the longitudinal direction between an extended position and a retracted position, wherein when the moveable tray member is in the extended position, the at least one lateral opening is arranged to admit tissue for extraction through the longitudinal passage of the tubular body;
   wherein, at the distal end, the first tubular body member comprises a plurality of longitudinally projecting portions separated by a plurality of spaces that are bordered by cutting surfaces of the first tubular body member; and
   wherein the steerable surgical device is configured to permit a portion of the moveable tray member to extend in the longitudinal direction beyond the plurality of longitudinally projecting portions when the moveable tray member is in the extended position.

2. The steerable surgical device of claim 1, further comprising a retractable tip member arrangeable at a distal end of the moveable tray member, wherein the retractable tip member is configured to be retracted through the moveable tray member and the longitudinal passage to exit the tubular body, and is further configured to be returned through the longitudinal passage and the moveable tray member to be positioned at the distal end of the moveable tray member.

3. The steerable surgical device of claim 2, wherein the retractable tip member has an associated guidewire extending in the longitudinal direction, to permit the retractable tip member to be retracted and returned by manipulation of the associated guidewire.

4. The steerable surgical device of claim 1, wherein:
   the at least one lateral opening of the moveable tray member comprises a plurality of lateral openings, with each lateral opening of the plurality of lateral openings being aligned with a corresponding space of the plurality of spaces.

5. The steerable surgical device of claim 1, wherein the plurality of tendon members comprises a plurality of shape memory alloy actuators.

6. The steerable surgical device of claim 1, wherein the first tubular joint member comprises a hyperelastic material.

7. The steerable surgical device of claim 1, wherein the first tubular joint member comprises a plurality of transverse slits extending perpendicular to the longitudinal direction, and the plurality of transverse silts comprises at least one first transverse slit, at least one second transverse slit oriented differently from the at least one first transverse slit, and at least one third transverse slit oriented differently from each of the at least one first transverse slit and the at least one second transverse slit.

8. The steerable surgical device of claim 1, wherein:
   the plurality of tubular body members further comprises a third tubular body member; and
   the steerable surgical device further comprises a second tubular joint member arranged between the second tubular body member and the third tubular body member.

9. The steerable surgical device of claim 1, wherein:
   each tendon member of the plurality of tendon members is arranged at a different angular position relative to the longitudinal axis; and
   the plurality of tendon members is anchored to a first group of anchor points arranged between the distal end and the first tubular joint member.

10. The steerable surgical device of claim 9, wherein each tendon member of the plurality of tendon members is looped around a corresponding anchor point of the first group of anchor points, such that each tendon member includes continuous first and second segments extending in parallel in the longitudinal direction.

11. A steerable surgical device comprising:
    a tubular body comprising: a central longitudinal axis extending in a longitudinal direction, a longitudinal passage, -a base end, -a distal end opposing the base end, and a plurality of transverse slits arranged closer to the distal end than to the base end, the plurality of transverse slits comprising at least one first transverse slit, at least one second transverse slit oriented differently from the at least one first transverse slit, and at least one third transverse slit oriented differently from each of the at least one first transverse slit and the at least one second transverse slit;

a first anchor point arranged between the at least one first transverse slit and the at least one second transverse slit, a second anchor point arranged between the at least one second transverse slit and the at least one third transverse slit, and a third anchor point arranged between the at least one third transverse slit and the distal end;

a first tendon member anchored to and extending from the first anchor point towards the base end, a second tendon member anchored to and extending from the second anchor point towards the base end, and a third tendon member anchored to and extending from the third anchor point towards the base end; and a moveable tray member arranged at the distal end, the moveable tray member comprising at least one lateral opening and being configured to translate in the longitudinal direction between an extended position and a retracted position, wherein when the moveable tray member is in the extended position, the at least one lateral opening is arranged to admit tissue for extraction through the longitudinal passage of the tubular body.

12. The steerable surgical device of claim 11, wherein the tubular body consists of a unitary body member in which the at least one first transverse slit, the at least one second transverse slit, and at least one third transverse slit are defined.

13. The steerable surgical device of claim 11, wherein the tubular body comprises a first body segment in which the at least one first transverse slit is defined, a second body segment in which the at least one second transverse slit is defined, and a third body segment in which the at least one third transverse slit is defined.

14. The steerable surgical device of claim 13, wherein:
at the distal end, the first body segment comprises a plurality of longitudinally projecting portions separated by a plurality of spaces that are bordered by cutting surfaces of the first body segment; and
the steerable surgical device is configured to permit a portion of the moveable tray member to extend in the longitudinal direction beyond the plurality of longitudinally projecting portions when the moveable tray member is in the extended position.

15. The steerable surgical device of claim 14, wherein:
the at least one lateral opening of the moveable tray member comprises a plurality of lateral openings, with each lateral opening of the plurality of lateral openings being aligned with a corresponding space of the plurality of spaces.

16. The steerable surgical device of claim 11, further comprising a retractable tip member arrangeable at a distal end of the moveable tray member, wherein the retractable tip member is configured to be retracted through the moveable tray member and the longitudinal passage to exit the tubular body, and the retractable tip member is further configured to be returned through the longitudinal passage and the moveable tray member in order to be positioned at the distal end of the moveable tray member.

17. The steerable surgical device of claim 16, wherein the retractable tip member has an associated guidewire extending in the longitudinal direction, to permit the retractable tip member to be retracted and returned by manipulation of the associated guidewire.

18. The steerable surgical device of claim 11, wherein each of the first tendon member, the second tendon member, and the third tendon member comprises a shape memory alloy actuator.

19. The steerable surgical device of claim 11, wherein each of the first tendon member, the second tendon member, and the third tendon member is arranged at a different angular position relative to the longitudinal axis.

20. A steerable surgical device comprising:
a tubular body comprising: a central longitudinal axis extending in a longitudinal direction, a base end, a distal end opposing the base end, a plurality of tubular body members including first and second tubular body members arranged between the base end and the distal end, a first tubular joint member arranged between the first tubular body member and the second tubular body member, and a longitudinal passage extending through at least the plurality of tubular body members and the first tubular joint member;

a plurality of tendon members extending from at least the first tubular body member through the first tubular joint member to the second tubular body member, wherein each tendon member of the plurality of tendon members is independently actuatable to effectuate pivotal movement between the first tubular body member and the second tubular body member; and a moveable tray member arranged at the distal end, the moveable tray member comprising at least one lateral opening and being configured to translate in the longitudinal direction between an extended position and a retracted position, wherein when the moveable tray member is in the extended position, the at least one lateral opening is arranged to admit tissue for extraction through the longitudinal passage of the tubular body;

wherein each tendon member of the plurality of tendon members is arranged at a different angular position relative to the longitudinal axis;

wherein the plurality of tendon members is anchored to a first group of anchor points arranged between the distal end and the first tubular joint member; and wherein each tendon member of the plurality of tendon members is looped around a corresponding anchor point of the first group of anchor points, such that each tendon member includes continuous first and second segments extending in parallel in the longitudinal direction.

* * * * *